US010952800B2

(12) United States Patent
Anglese

(10) Patent No.: US 10,952,800 B2
(45) Date of Patent: Mar. 23, 2021

(54) ARTICULATION ASSEMBLY FOR A SURGICAL INSTRUMENT SUCH AS FOR USE IN A ROBOTIC SURGICAL SYSTEM AND METHODS OF ASSEMBLING THE SAME

(71) Applicant: COVIDIEN LP, Mansfield, MA (US)

(72) Inventor: Kurt J. Anglese, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 76 days.

(21) Appl. No.: 16/395,748

(22) Filed: Apr. 26, 2019

(65) Prior Publication Data

US 2020/0337787 A1 Oct. 29, 2020

(51) Int. Cl.
| | |
|---|---|
| *A61B 34/30* | (2016.01) |
| *A61B 17/295* | (2006.01) |
| *B25J 9/10* | (2006.01) |
| *A61B 34/00* | (2016.01) |
| *A61B 17/00* | (2006.01) |

(52) U.S. Cl.
CPC ............ *A61B 34/30* (2016.02); *A61B 17/295* (2013.01); *B25J 9/104* (2013.01); *A61B 2017/00526* (2013.01); *A61B 2034/302* (2016.02); *A61B 2034/715* (2016.02)

(58) Field of Classification Search
CPC ... A62B 2034/715; A62B 34/30; A62B 34/71; B25J 9/104; F16H 25/20; F16H 2025/2053
See application file for complete search history.

(56) References Cited

U.S. PATENT DOCUMENTS

| 5,752,973 A | 5/1998 | Kieturakis |
| 5,792,135 A | 8/1998 | Madhani et al. |
| 5,848,986 A | 12/1998 | Lundquist et al. |

(Continued)

FOREIGN PATENT DOCUMENTS

| KR | 20180104452 A | * | 9/2018 | ............. A62B 34/30 |
| WO | 2016137611 A1 | | 9/2016 | |

(Continued)

OTHER PUBLICATIONS

Extended European Search Report issued in corresponding European Application No. 20167605.3 dated Sep. 15, 2020, 24 pages.

*Primary Examiner* — Thomas C Diaz
(74) *Attorney, Agent, or Firm* — Carter, DeLuca & Farrell LLP

(57) ABSTRACT

A surgical instrument articulation assembly includes a lead screw sub-assembly including four lead screws. A first gear sub-assembly includes first and second gears coupled to the first and third lead screws. A second gear sub-assembly includes third and fourth gears coupled to the second and fourth lead screws, respectively, a first compound gear including a distal gear coupling the first and second gears with one another, and a proximal gear coupled with a first coupling gear disposed about a first input. The third gear sub-assembly includes a second compound gear including a distal gear coupling the third and fourth gears with one another, and a proximal gear coupled with a second coupling gear disposed about a second input. A rotational input provided to the first or second input respectively rotates the first and third lead screws and or the second and fourth lead screws.

13 Claims, 19 Drawing Sheets

(56) References Cited

U.S. PATENT DOCUMENTS

| | | | |
|---|---|---|---|
| 6,817,974 B2 | 11/2004 | Cooper et al. | |
| 7,799,028 B2 | 9/2010 | Schechter et al. | |
| 7,861,906 B2 | 1/2011 | Doll et al. | |
| 7,918,230 B2* | 4/2011 | Whitman | A61B 17/068 |
| | | | 128/898 |
| 8,579,176 B2 | 11/2013 | Smith et al. | |
| 9,055,961 B2 | 6/2015 | Manzo et al. | |
| 9,474,569 B2 | 10/2016 | Manzo et al. | |
| 2002/0099371 A1 | 7/2002 | Schulze et al. | |
| 2002/0177842 A1 | 11/2002 | Weiss | |
| 2003/0125734 A1 | 7/2003 | Mollenauer | |
| 2003/0208186 A1 | 11/2003 | Moreyra | |
| 2006/0022015 A1 | 2/2006 | Shelton et al. | |
| 2006/0025811 A1 | 2/2006 | Shelton | |
| 2007/0233052 A1 | 10/2007 | Brock | |
| 2008/0015631 A1 | 1/2008 | Lee et al. | |
| 2010/0274265 A1 | 10/2010 | Wingardner et al. | |
| 2010/0292691 A1 | 11/2010 | Brogna | |
| 2011/0118707 A1 | 5/2011 | Burbank | |
| 2011/0118708 A1 | 5/2011 | Burbank et al. | |
| 2011/0118709 A1 | 5/2011 | Burbank | |
| 2011/0118754 A1 | 5/2011 | Dachs, II et al. | |
| 2011/0185834 A1 | 8/2011 | Pratt | |
| 2018/0028271 A1* | 2/2018 | Rockrohr | A61B 34/30 |

FOREIGN PATENT DOCUMENTS

| | | |
|---|---|---|
| WO | 2017053507 A1 | 3/2017 |
| WO | 2017181153 A1 | 10/2017 |
| WO | 2018041218 A1 | 3/2018 |
| WO | 2018207136 A1 | 11/2018 |

\* cited by examiner

ARTICULATION ASSEMBLY FOR A SURGICAL INSTRUMENT SUCH AS FOR USE IN A ROBOTIC SURGICAL SYSTEM AND METHODS OF ASSEMBLING THE SAME

FIELD

The present disclosure relates to surgical instruments and, more specifically, to articulation assemblies for surgical instruments such as, for example, for use in robotic surgical systems, and methods of assembling the same.

BACKGROUND

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

The number, type, and configuration of inputs provided by the robotic arm of a robotic surgical system are constraints in the design of surgical instruments configured for use with the robotic surgical system. That is, in designing a surgical instrument compatible for mounting on and use with the robotic arm of a robotic surgical system, consideration should be taken in determining how to utilize the available inputs provided by the robotic arm to achieve the desired functionality of the surgical instrument.

SUMMARY

As used herein, the term "distal" refers to the portion that is being described which is further from a surgeon, while the term "proximal" refers to the portion that is being described which is closer to a surgeon. The terms "about," substantially," and the like, as utilized herein, are meant to account for manufacturing, material, environmental, use, and/or measurement tolerances and variations. Further, to the extent consistent, any of the aspects described herein may be used in conjunction with any or all of the other aspects described herein.

Provided in accordance with aspects of the present disclosure is an articulation assembly for a surgical instrument including a lead screw sub-assembly and first, second, and third gear sub-assemblies. The lead screw sub-assembly includes first, second, third, and fourth lead screws. The first and third lead screws are diagonally-opposite one another and the second and fourth lead screws are diagonally-opposite one another. The first gear sub-assembly includes a first housing at least partially capturing first and second gears therein. The first and second gears are coupled to the first and third lead screws. The second gear sub-assembly is configured to engage the first gear sub-assembly and includes a second housing at least partially capturing third and fourth gears, a first central compound gear, and a first coupling gear disposed about a first input. The third and fourth gears are coupled to the second and fourth lead screws, respectively. The first central compound gear includes a distal gear and a proximal gear. The distal gear couples the first and second gears with one another, thereby coupling the first and third lead screws with one another. The first coupling gear is coupled with the proximal gear, while the first input extends proximally from the second housing.

The third gear sub-assembly is configured to engage the second gear sub-assembly and includes a third housing at least partially capturing a second central compound gear and a second coupling gear disposed about a second input. The second central compound gear includes a distal gear and a proximal gear. The distal gear couples the third and fourth gears with one another, thereby coupling the second and fourth lead screws with one another. The second coupling gear is coupled with the proximal gear, while the second input extends proximally from the third housing. The first input extends proximally through and from the third housing. A rotational input provided to the first input rotates the first and third lead screws, and a rotational input provided to the second input rotates the second and fourth lead screws.

In an aspect of the present disclosure, each of the first, second, third, and fourth lead screws includes a collar engaged thereon and an articulation cable coupled to the collar. Rotation of one of the first, second, third, or fourth lead screws translates the corresponding collar to tension or un-tension the corresponding articulation cable.

In another aspect of the present disclosure, the first and third lead screws define opposite pitch such that a rotational input provided to the first input tensions one of the corresponding articulation cables and un-tensions the other corresponding articulation cable. Similarly, the second and fourth lead screws define opposite pitch such that a rotational input provided to the second input tensions one of the corresponding articulation cables and un-tensions the other corresponding articulation cable.

In another aspect of the present disclosure, the first housing of the first gear sub-assembly includes proximal and distal housing bodies at least partially capturing the first and second gears therebetween.

In still another aspect of the present disclosure, the first and second gears are coupled to the first and third lead screws via respective first and second outputs engaged with the first and second gears, respectively, and extending distally from the first housing to couple to the first and third lead screws.

In another aspect of the present disclosure, the second housing of the second gear sub-assembly includes proximal and distal housing bodies at least partially capturing the third and fourth gears, the first central compound gear, and the first coupling gear therebetween.

In yet another aspect of the present disclosure, the third and fourth gears are coupled to the second and fourth lead screws via respective third and fourth outputs engaged with the third and fourth gears, respectively, and extending distally from the second housing body through the first housing to couple to the second and fourth lead screws.

In another aspect of the present disclosure, the third housing of the third gear sub-assembly includes proximal and distal housing bodies at least partially capturing the second central compound gear and the second coupling gear therebetween, In still yet another aspect of the present disclosure, the first, second, and third housings are configured to stack relatively to one another in a distal-to-proximal orientation.

In another aspect of the present disclosure, at least one first engagement arm engages the first and second housings with one another and/or at least one second engagement arm engages the second and third housings with one another.

Another articulation mechanism for a surgical instrument provided in accordance with the present disclosure includes a lead screw sub-assembly and first, second, and third gear sub-assemblies. The lead screw sub-assembly includes first, second, third, and fourth lead screws wherein the first and third lead screws define opposite pitch and are diagonally-opposite one another and wherein the second and fourth lead screws define opposite pitch and are diagonally-opposite one another. Each of the first, second, third, and fourth lead screws includes a collar engaged thereon and an articulation cable coupled to the collar. Rotation of one of the first, second, third, or fourth lead screws translates the corresponding collar to tension or un-tension the corresponding articulation cable.

The first gear sub-assembly includes first and second gears disposed about first and second outputs, respectively, and proximal and distal housing bodies capturing the first and second gears therebetween. The first and second outputs extend distally from the distal housing body to couple to the first and third lead screws.

The second gear sub-assembly is configured to engage the first gear sub-assembly and includes third and fourth gears disposed about third and fourth outputs, respectively, a first central compound gear, a first coupling gear disposed about a first input, and proximal and distal housing bodies at least partially capturing the third and fourth gears, the first central compound gear, and the first coupling gear therebetween. The third and fourth outputs extend distally from the distal housing body of the second gear sub-assembly and through the first gear sub-assembly to couple to the second and fourth lead screws, respectively. The first central compound gear includes a distal gear and a proximal gear. The distal gear is configured to extend into the first gear sub-assembly and engage the first and second gears with one another, thereby coupling the first and third lead screws with one another. The first coupling gear is coupled with the proximal gear. The first input extends proximally from the proximal housing body of the second gear sub-assembly.

The third gear sub-assembly is configured to engage the second gear sub-assembly and includes a second central compound gear, a second coupling gear disposed about a second input, and proximal and distal housing bodies at least partially capturing the second compound gear and the second coupling gear therebetween. The second central compound gear includes a distal gear and a proximal gear. The distal gear is configured to extend into the second gear sub-assembly and engage the third and fourth gears with one another, thereby coupling the second and fourth lead screws with one another. The second coupling gear is coupled with the proximal gear. The second input extends proximally from the proximal housing body of the third gear sub-assembly. The first input extends proximally through the third gear sub-assembly. A rotational input provided to the first input rotates the first and second lead screws to tension or un-tension the first and third articulation cables, and a rotational input provided to the second input rotates the second and fourth lead screws to tension or un-tension the second and fourth articulation cables.

In an aspect of the present disclosure, the articulation assembly further includes a plurality of dowels extending through the collars and the first, second and third gear sub-assemblies. In such aspects, the lead screw assembly may further include a distal plate wherein the plurality of dowels are engaged with the distal plate.

A method of assembling an articulation assembly for a surgical instrument in accordance with the present disclosure includes moving a first gear sub-assembly into engagement with a lead screw sub-assembly including first, second, third, and fourth lead screws such that first and second gears of the first gear sub-assembly are coupled with the first and third lead screws, respectively. The method further includes moving a second gear sub-assembly into engagement with the first gear sub-assembly such that third and fourth gears of the second gear sub-assembly are coupled with the second and fourth lead screws, respectively, and such that a distal gear of a first central compound gear of the second gear sub-assembly couples the first and second gears of the first gear sub-assembly with one another, thereby coupling the first and third lead screws with one another. The method additionally includes moving a third gear sub-assembly into engagement with the second gear sub-assembly such that a distal gear of a second central compound gear of the third gear sub-assembly couples the third and fourth gears of the second gear sub-assembly with one another, thereby coupling the second and fourth lead screws with one another.

In an aspect of the present disclosure, moving at least one of the first, second, or third gear sub-assemblies includes sliding the at least one of the first, second, or third gear sub-assemblies along a plurality of dowels.

In another aspect of the present disclosure, moving the second gear sub-assembly into engagement with the first gear sub-assembly includes engaging a second housing of the second gear sub-assembly with a first housing of the first gear sub-assembly. Additionally or alternatively, moving the third gear sub-assembly into engagement with the second gear sub-assembly includes engaging a third housing of the third gear sub-assembly with the second housing of the second gear sub-assembly.

In yet another aspect of the present disclosure, the method further includes coupling a first input shaft to a first input proximally of the third gear sub-assembly. The first input extends distally through the third gear sub-assembly to the second gear sub-assembly, wherein the first input mounts a first coupling gear thereon. The first coupling gear couples to a proximal gear of the first central compound gear. Additionally or alternatively, the method further includes coupling a second input shaft to a second input proximally of the third gear sub-assembly. The second input extends distally to the third gear sub-assembly, wherein the second input mounts a second coupling gear thereon. The second coupling gear is coupled to a proximal gear of the second central compound gear.

In still yet another aspect of the present disclosure, the method further includes pre-tensioning first and third articulation cables associated with the first and third lead screws after moving the first gear sub-assembly into engagement with the lead screw sub-assembly and prior to moving the second gear sub-assembly into engagement with the first gear sub-assembly. The method may additionally or alternatively include pre-tensioning second and fourth articulation cables associated with the second and fourth lead screws after moving the second gear sub-assembly into engagement with the first gear sub-assembly and prior to moving the third gear sub-assembly into engagement with the second gear sub-assembly.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
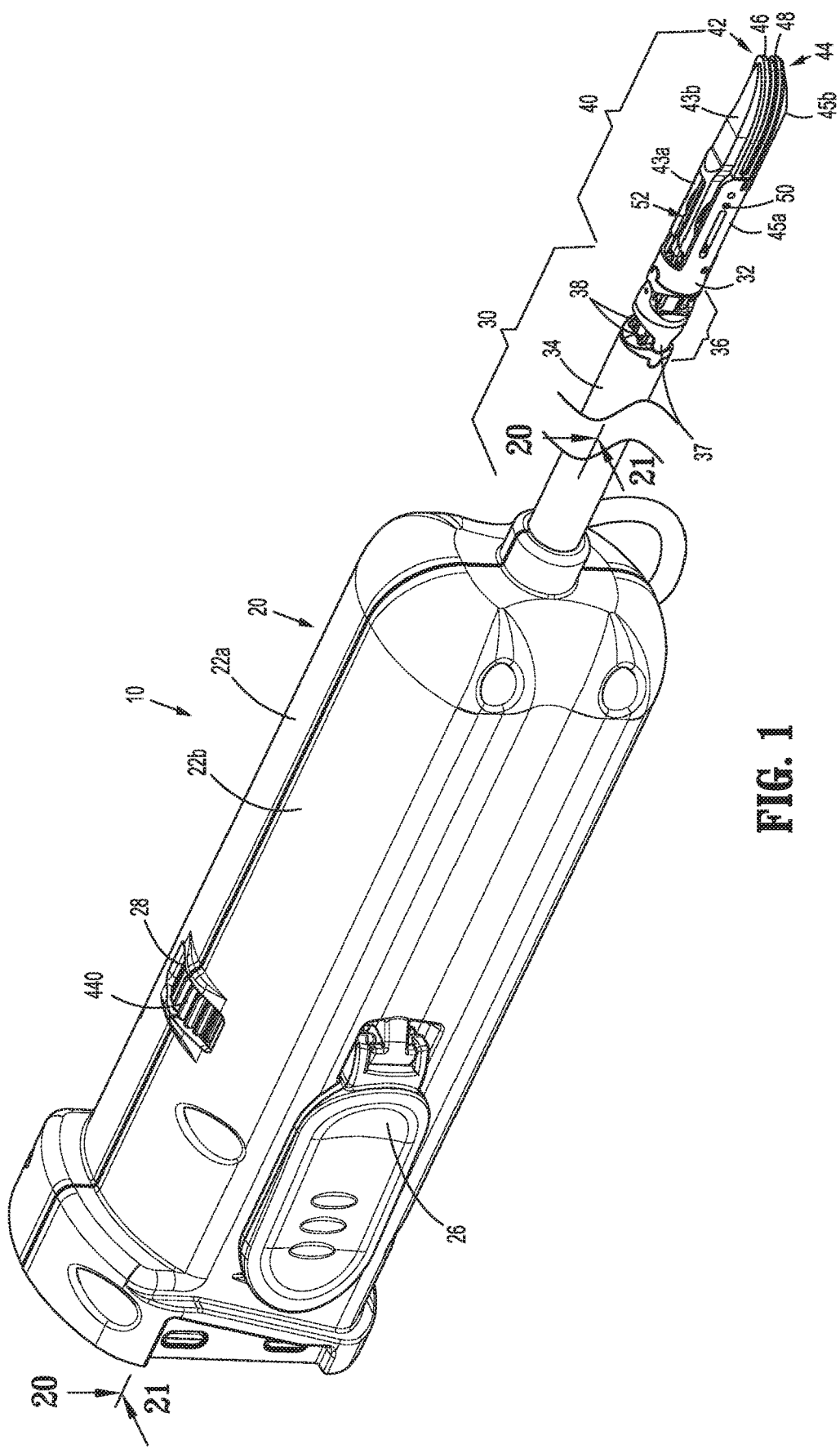
FIG. 1 is a perspective view of a surgical instrument provided in accordance with the present disclosure configured for mounting on a robotic arm of a robotic surgical system.
Figure 2A:
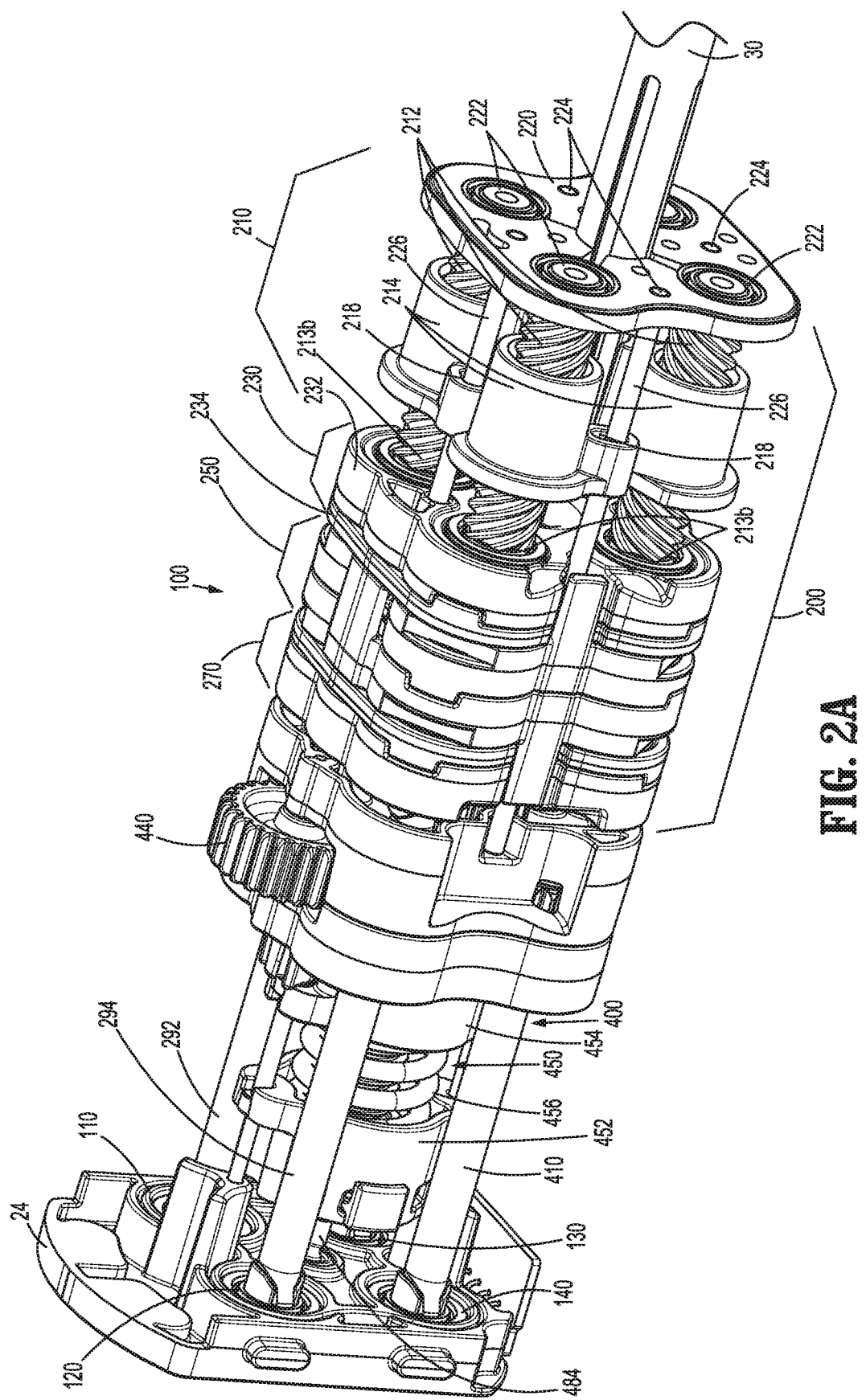
FIG. 2A is a front, perspective view of a proximal portion of the surgical instrument of FIG. 1 with an outer housing removed.
Figure 2B:
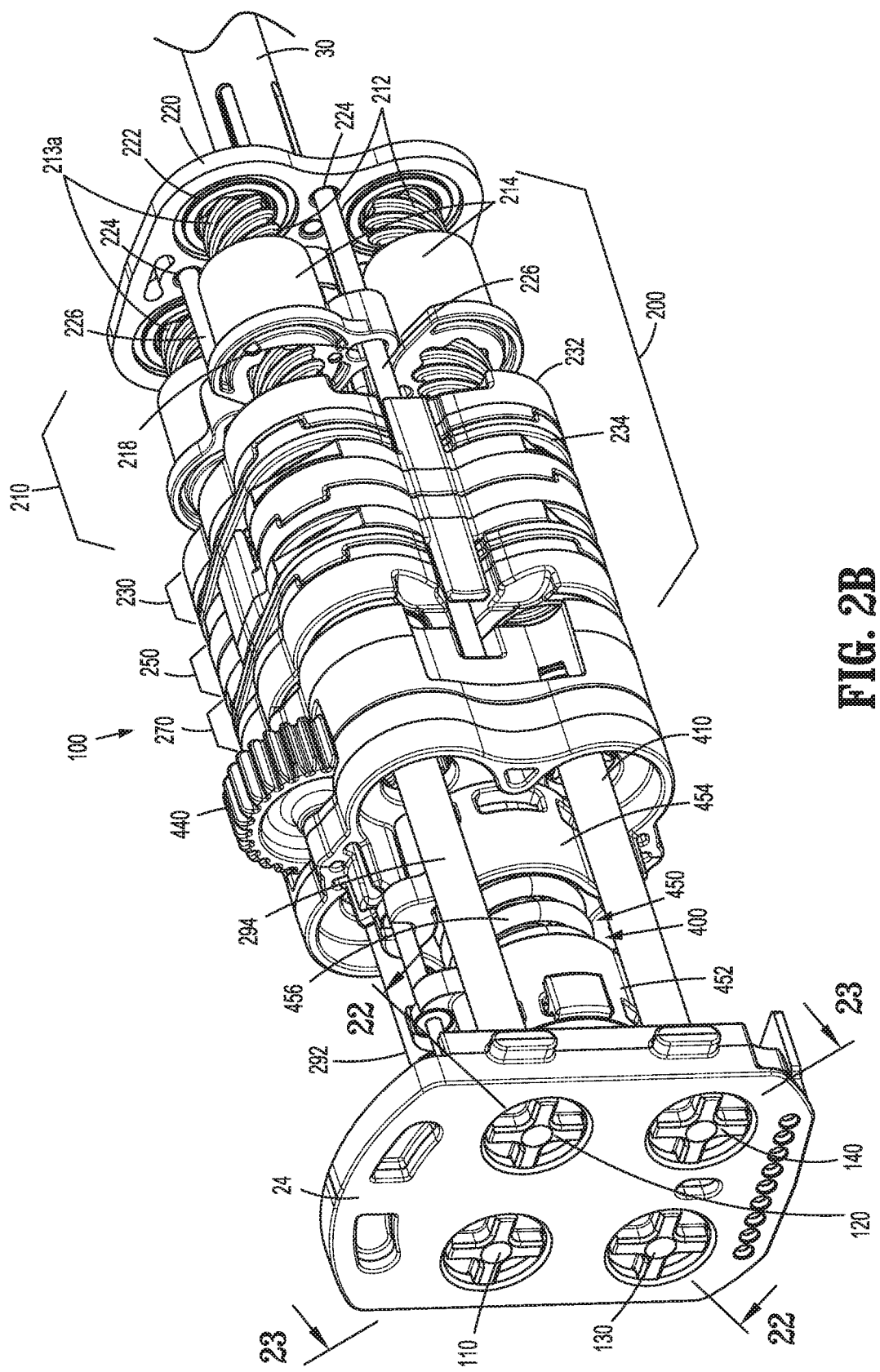
FIG. 2B is a rear, perspective view of the proximal portion of the surgical instrument of FIG. 1 with the outer housing removed.
Figure 3:
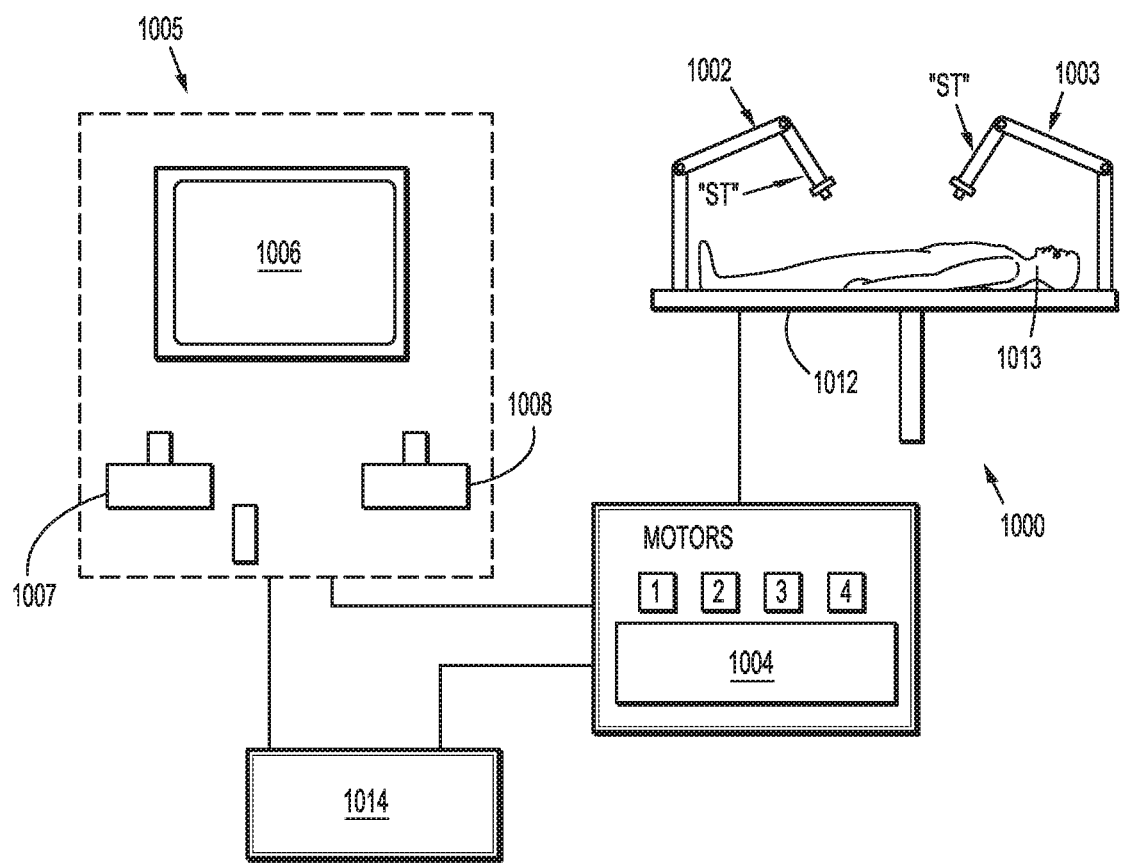
FIG. 3 is a schematic illustration of an exemplary robotic surgical system configured to releasably receive the surgical instrument of FIG. 1.

Referring to FIGS. 1-2B, a surgical instrument 10 provided in accordance with the present disclosure generally includes a housing 20, a shaft 30 extending distally from housing 20, and end effector assembly 40 extending distally from shaft 30, and a gearbox 100 disposed within housing 20 and operably associated with shaft 30 and end effector assembly 40. Instrument 10 is detailed herein as an articulating electrosurgical forceps configured for use with a robotic surgical system, e.g., robotic surgical system 1000 (FIG. 3). However, the aspects and features of instrument 10 provided in accordance with the present disclosure, detailed below, are equally applicable for use with other suitable surgical instruments and/or in other suitable surgical systems.

Housing 20 of instrument 10 includes first and second body portion 22a, 22b and a proximal face plate 24 that cooperate to enclose gearbox 100 therein. Proximal face plate 24 includes apertures defined therein through which inputs 110-140 of gearbox 100 extend. A pair of latch levers 26 (only one of which is illustrated in FIG. 1) extends outwardly from opposing sides of housing 20 and enables releasable engagement of housing 20 with a robotic arm of a surgical system, e.g., robotic surgical system 1000 (FIG. 3). An aperture 28 defined through housing 20 permits thumbwheel 440 to extend therethrough to enable manual manipulation of thumbwheel 440 from the exterior of housing 20 to permit manual opening and closing of end effector assembly 40.

Shaft 30 of instrument 10 includes a distal segment 32, a proximal segment 34, and an articulating section 36 disposed between the distal and proximal segments 32, 34, respectively. Articulating section 36 includes one or more articulating components 37, e.g., links, joints, etc. A plurality of articulation cables 38, e.g., four (4) articulation cables, or other suitable actuators, extends through articulating section 36. More specifically, articulation cables 38 are operably coupled to distal segment 32 of shaft 30 at the distal ends thereof and extend proximally from distal segment 32 of shaft 30, through articulating section 36 of shaft 30 and proximal segment 34 of shaft 30, and into housing 20, wherein articulation cables 38 operably couple with an articulation assembly 200 of gearbox 100 to enable selective articulation of distal segment 32 (and, thus end effector assembly 40) relative to proximal segment 34 and housing 20, e.g., about at least two axes of articulation (yaw and pitch articulation, for example). Articulation cables 38 are arranged in a generally rectangular configuration, although other suitable configurations are also contemplated.

With respect to articulation of end effector assembly 40 relative to proximal segment 34 of shaft 30, actuation of articulation cables 38 is effected in pairs. More specifically, in order to pitch end effector assembly 40, the upper pair of cables 38 is actuated in a similar manner while the lower pair of cables 38 is actuated in a similar manner relative to one another but an opposite manner relative to the upper pair of cables 38. With respect to yaw articulation, the right pair of cables 38 is actuated in a similar manner while the left pair of cables 38 is actuated in a similar manner relative to one another but an opposite manner relative to the right pair of cables 38.

With reference to FIG. 1, end effector assembly 40 includes first and second jaw members 42, 44, respectively. Each jaw member 42, 44 includes a proximal flange portion 43a, 45a and a distal body portion 43b, 45b, respectively. Distal body portions 43b, 45b define opposed tissue-contacting surfaces 46, 48, respectively. Proximal flange portions 43a, 45a are pivotably coupled to one another about a pivot 50 and are operably coupled to one another via a cam-slot assembly 52 including a cam pin slidably received within cam slots defined within the proximal flange portion 43a, 45a of at least one of the jaw members 42, 44, respectively, to enable pivoting of jaw member 42 relative to jaw member 44 and distal segment 32 of shaft 30 between a spaced-apart position (e.g., an open position of end effector assembly 40) and an approximated position (e.g. a closed position of end effector assembly 40) for grasping tissue between tissue-contacting surfaces 46, 48. As an alternative to this unilateral configuration, a bilateral configuration may be provided whereby both jaw members 42, 44 are pivotable relative to one another and distal segment 32 of shaft 30.

In embodiments, longitudinally-extending knife channels (not shown) are defined through tissue-contacting surfaces 46, 48, respectively, of jaw members 42, 44. In such embodiments, a knife assembly including a knife tube 62 (FIGS. 7 and 20-23) extends from housing 20 through shaft 30 to end effector assembly 40 and a knife blade (not shown) disposed within end effector assembly 40 between jaw members 42, 44 is provided to enable cutting of tissue grasped between tissue-contacting surfaces 46, 48 of jaw members 42, 44, respectively. Knife tube 62 (FIGS. 7 and 20-23) is operably coupled to a knife drive assembly 300 of gearbox 100 (FIGS. 2A and 2B) at a proximal end thereof to enable selective actuation thereof to, in turn, reciprocate the knife blade (not shown) between jaw members 42, 44 to cut tissue grasped between tissue-contacting surfaces 46, 48.

Referring also to FIGS. 2A and 2B, a drive rod 484 is operably coupled to cam-slot assembly 52 of end effector assembly 40, e.g., engaged with the cam pin thereof, such that longitudinal actuation of drive rod 484 (FIGS. 7 and 20-23) pivots jaw member 42 relative to jaw member 44 between the spaced-apart and approximated positions. More specifically, urging drive rod 484 proximally pivots jaw member 42 relative to jaw member 44 towards the approximated position while urging drive rod 484 distally pivots jaw member 42 relative to jaw member 44 towards the spaced-apart position. However, other suitable mechanisms and/or configurations for pivoting jaw member 42 relative to jaw member 44 between the spaced-apart and approximated positions in response to selective actuation of drive rod 484 are also contemplated. Drive rod 484 extends proximally from end effector assembly 40 through shaft 30 and into housing 20 wherein drive rod 484 is operably coupled with a jaw drive assembly 400 of gearbox 100 (FIGS. 2A and 2B) to enable selective actuation of end effector assembly 40 to grasp tissue therebetween and apply a closure force within an appropriate jaw closure force range, as detailed below.

Tissue-contacting surfaces 46, 48 of jaw members 42, 44, respectively, are at least partially formed from an electrically conductive material and are energizable to different potentials to enable the conduction of electrical energy through tissue grasped therebetween, although tissue-contacting surfaces 46, 48 may alternatively be configured to supply any suitable energy, e.g., thermal, microwave, light, ultrasonic, ultrasound, etc., through tissue grasped therebetween for energy-based tissue treatment. Instrument 10 defines a conductive pathway (not shown) through housing 20 and shaft 30 to end effector assembly 40 that may include lead wires, contacts, and/or electrically-conductive components to enable electrical connection of tissue-contacting surfaces 46, 48 of jaw members 42, 44, respectively, to an energy source (not shown), e.g., an electrosurgical generator, for supplying energy to tissue-contacting surfaces 46, 48 to treat, e.g., seal, tissue grasped between tissue-contacting surfaces 46, 48.

With additional reference to FIGS. 2A and 2B, as noted above, gearbox 100 is disposed within housing 20 and includes an articulation assembly 200, a knife drive assembly 300, and a jaw drive assembly 400. Articulation assembly 200, as described in greater detail below, is operably coupled between first and second inputs 110, 120, respectively, of gearbox 100 and articulation cables 38 (FIG. 1) such that, upon receipt of appropriate rotational inputs into first and/or second inputs 110, 120, articulation assembly 200 manipulates cables 38 (FIG. 1) to articulate end effector assembly 40 in a desired direction, e.g., to pitch and/or yaw end effector assembly 40. Knife drive assembly 300, as also described in greater detail below, is operably coupled between third input 130 of gearbox 100 and knife tube 62 (FIGS. 20-23) such that, upon receipt of appropriate rotational input into third input 130, knife drive assembly 300 manipulates knife tube 62 (FIGS. 20-23) to reciprocate the knife blade (not shown) between jaw members 42, 44 to cut tissue grasped between tissue-contacting surfaces 46, 48. Jaw drive assembly 400, as still further described in greater detail below, is operably coupled between fourth input 140 of gearbox 100 and drive rod 484 such that, upon receipt of appropriate rotational input into fourth input 140, jaw drive assembly 400 pivots jaw members 42, 44 between the spaced-apart and approximated positions to grasp tissue therebetween and apply a closure force within an appropriate closure force range.

Gearbox 100 is configured to operably interface with a robotic surgical system 1000 (FIG. 3) when instrument 10 is mounted on robotic surgical system 1000 (FIG. 4), to enable robotic operation of gearbox 100 to provide the above-detailed functionality. That is, robotic surgical system 1000 (FIG. 3) selectively provides rotational inputs to inputs 110-140 of gearbox 100 to articulate end effector assembly 40, grasp tissue between jaw members 42, 44, and/or cut tissue grasped between jaw members 42, 44. However, it is also contemplated that gearbox 100 be configured to interface with any other suitable surgical system, e.g., a manual surgical handle, a powered surgical handle, etc. For the purposes herein, robotic surgical system 1000 (FIG. 3) is generally described.

Turning to FIG. 3, robotic surgical system 1000 is configured for use in accordance with the present disclosure. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and a mounted device which may be, for example, a surgical tool "ST." One or more of the surgical tools "ST" may be instrument 10 (FIG. 1), thus providing such functionality on a robotic surgical system 1000.

Robot arms 1002, 1003 may be driven by electric drives, e.g., motors, connected to control device 1004. Control device 1004, e.g., a computer, may be configured to activate the motors, in particular by means of a computer program, in such a way that robot arms 1002, 1003, and, thus, their mounted surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

With general reference to FIGS. 2A, 2B, and 4-19, articulation assembly 200 of gearbox 100 generally including a lead screw sub-assembly 210, a first gear sub-assembly 230, a second gear sub-assembly 250, a third gear sub-assembly 270, and first and second input shafts 292, 294. Although articulation assembly 200 is detailed below as including a plurality of gears, such gearing components may be replaced or supplemented with the use of belts instead of directly meshed gears, without departing from the present disclosure. Further, in embodiments, multiple gears (and/or belts) may be provided in place of single gears (and/or belts) to provide a desired amplification or attenuation effect.

Referring initially to FIGS. 2A, 2B, and 7-9, lead screw sub-assembly 210 includes four lead screws 212. Lead screws 212 are arranged to define a generally square configuration such that each lead screw 212 includes two adjacent lead screws 212, e.g., a vertically-adjacent lead screw 212 and a horizontally-adjacent lead screw 212, and a diagonally-opposed lead screw 212. The lead screws 212 of each diagonally-opposed pair of lead screws 212 define opposite thread-pitch directions.

Each lead screw 212 includes a collar 214 threadingly engaged thereabout such that rotation of the lead screw 212 translates the corresponding collar 214 longitudinally therealong. Each collar 214, in turn, includes a ferrule 216 (FIGS. 22 and 23) configured to engage a proximal end portion of one of the articulation cables 38 (FIGS. 22 and 23), e.g., via a crimped hook-slot engagement or other suitable engagement (mechanical fastening, adhesion, welding, etc.). Thus, distal translation of a collar 214 slackens the corresponding articulation cable 38 (FIGS. 22 and 23) by pushing the corresponding articulation cable 38 (FIGS. 22 and 23) in a distal direction, while proximal translation of a collar 214 tensions the corresponding articulation cable 38 (FIGS. 22 and 23) by pulling the corresponding articulation cable 38 (FIGS. 22 and 23) in a proximal direction. Collars 214 further include slots 218 defined therein, the purposes of which are detailed below.

Lead screw sub-assembly 210 further includes a distal plate 220 including four bushings 222 each of which rotatably retains the distal end portion 213a of one of the four lead screws 212. Proximal end portions 213b of lead screws 212 define keyed, e.g., semi-circular, inputs, such that rotational inputs to proximal end portions 213b rotate the lead screws 212. Distal plate 220 additionally defines four apertures 224 therein. Each aperture 224 is aligned with the slot 218 of one of the collars 214. A dowel 226 extends through each pair of aligned slots 218 and apertures 224 to thereby guide translation of collars 214 along lead screws 212 and inhibit rotation of collars 214.

Figure 7:
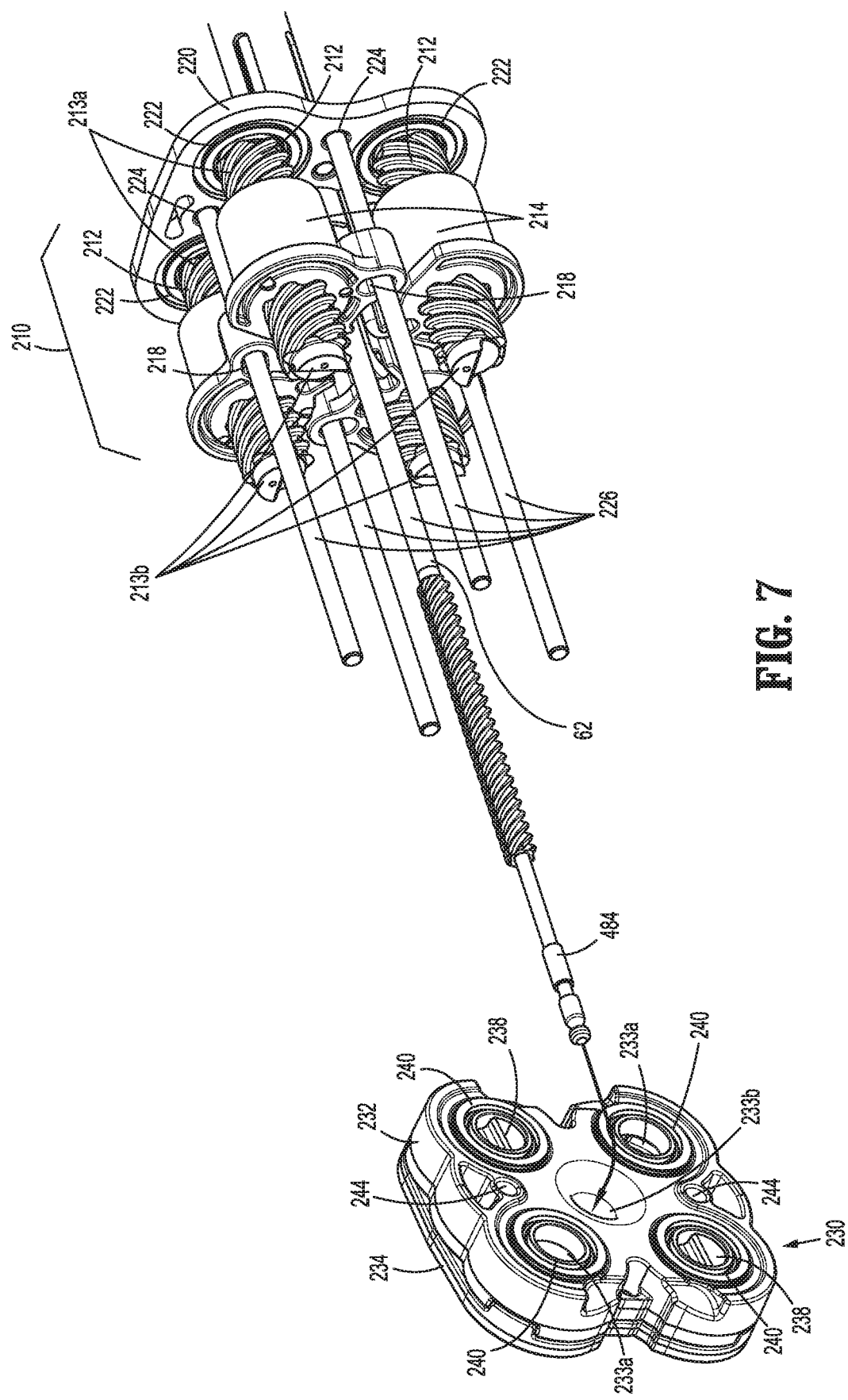
FIG. 7 is an exploded, perspective view illustrating assembly of the first gear sub-assembly of FIG. 4 with a lead screw sub-assembly of the articulation assembly of the gearbox of the surgical instrument of FIG. 1.

With momentary reference to FIG. 7, lead screw sub-assembly 210 is configured to receive knife tube 62, including drive rod 484 therein, through a center portion thereof such that knife tube 62 and drive rod 484 extend centrally between lead screws 212 and collars 214 without interference.

Figure 4:
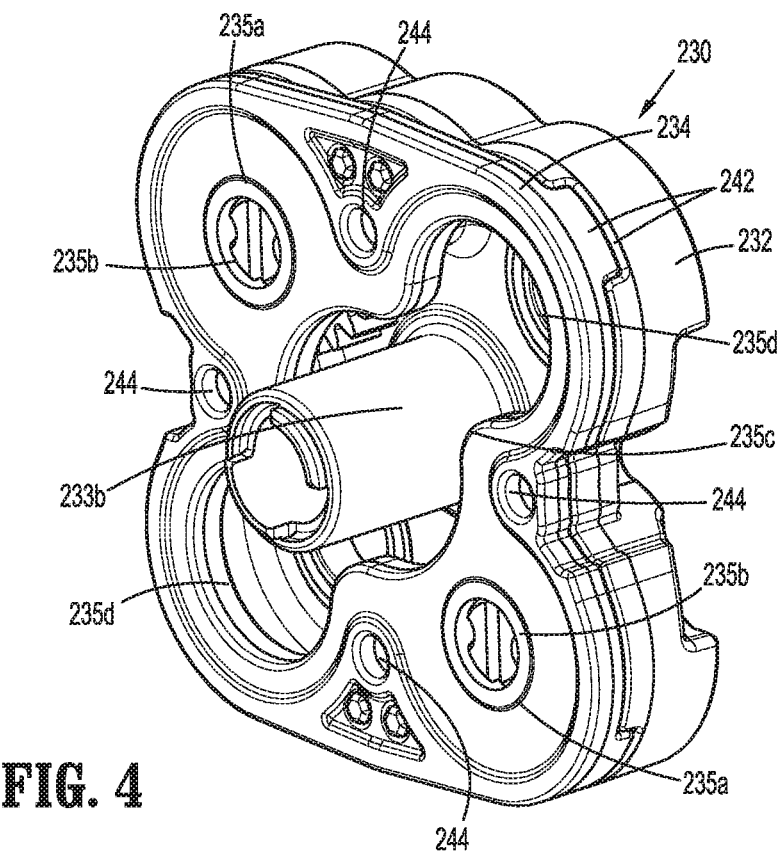
FIG. 4 is a rear, perspective view of a first gear sub-assembly of an articulation assembly of the gearbox of the surgical instrument of FIG. 1.
Figure 5:
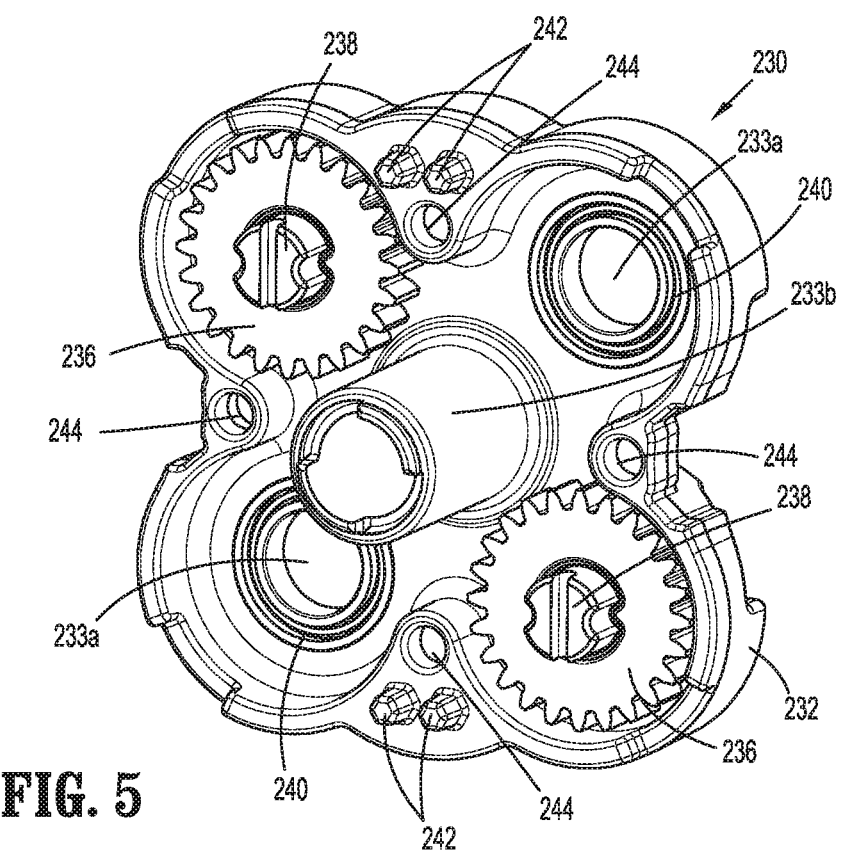
FIG. 5 is a rear, perspective view of the first gear sub-assembly of FIG. 4 with the proximal housing body thereof removed.
Figure 6:
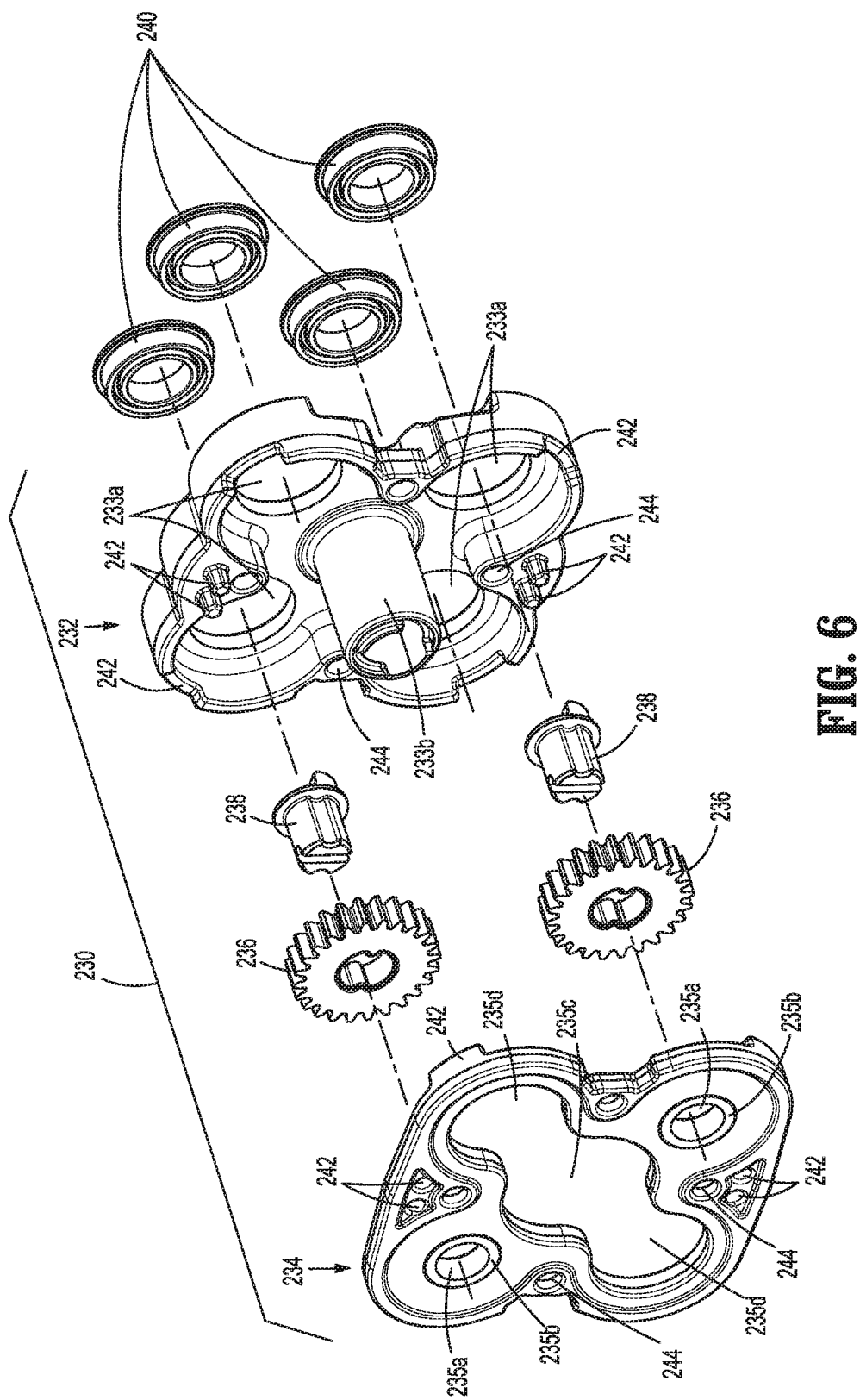
FIG. 6 is an exploded, perspective view of the first gear sub-assembly of FIG. 4.

Referring to FIGS. 4-6, first gear sub-assembly 230 includes a distal housing body 232, a proximal housing body 234, and a pair of diagonally-opposed gears 236 mounted on keyed outputs 238. Distal housing body 232 defines four apertures 233a arranged to define a generally square configuration. A bushing 240 may be retained within each aperture 233a. Distal housing body 232 further defines a central tube 233b extending proximally therefrom.

Proximal housing body 234 defines a pair of diagonally-opposed apertures 235a each of which may include a bushing 235b disposed therein. Proximal housing body 234 further defines a central opening 235c that is configured to receive central tube 233b therethrough and a second pair of diagonally-opposed apertures 235d (which may communicate with central opening 235c as shown or may be separate therefrom). Distal housing body 232 and proximal housing body 234 include cooperating male-female components 242 to facilitate engagement of distal housing body 232 and proximal housing body 234 with one another, although other suitable engagements are also contemplated.

Gears 236 are rotatably captured between distal housing body 232 and proximal housing body 234. Keyed outputs 238 include gears 236 mounted thereon such that rotation of one of the gears 236 rotates the corresponding keyed output 238. Each keyed output 238 extends distally into one of bushings 240. The distal end portions of keyed outputs 238 define keyed, e.g., semi-circular, outputs to enable rotational output therefrom. The proximal end portions of keyed outputs 238 are rotatably supported within bushings 235b.

Figure 8:
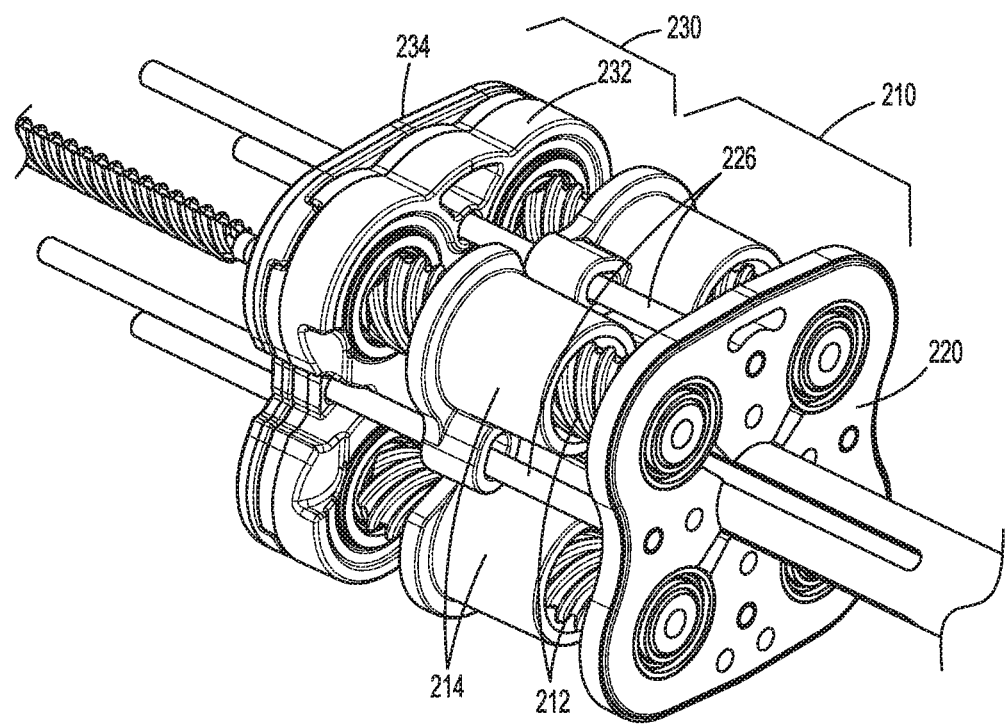
FIG. 8 is a front, perspective view of the first gear sub-assembly of FIG. 4 assembled on the lead screw sub-assembly of FIG. 7 to partially assemble the articulation assembly.
Figure 9:
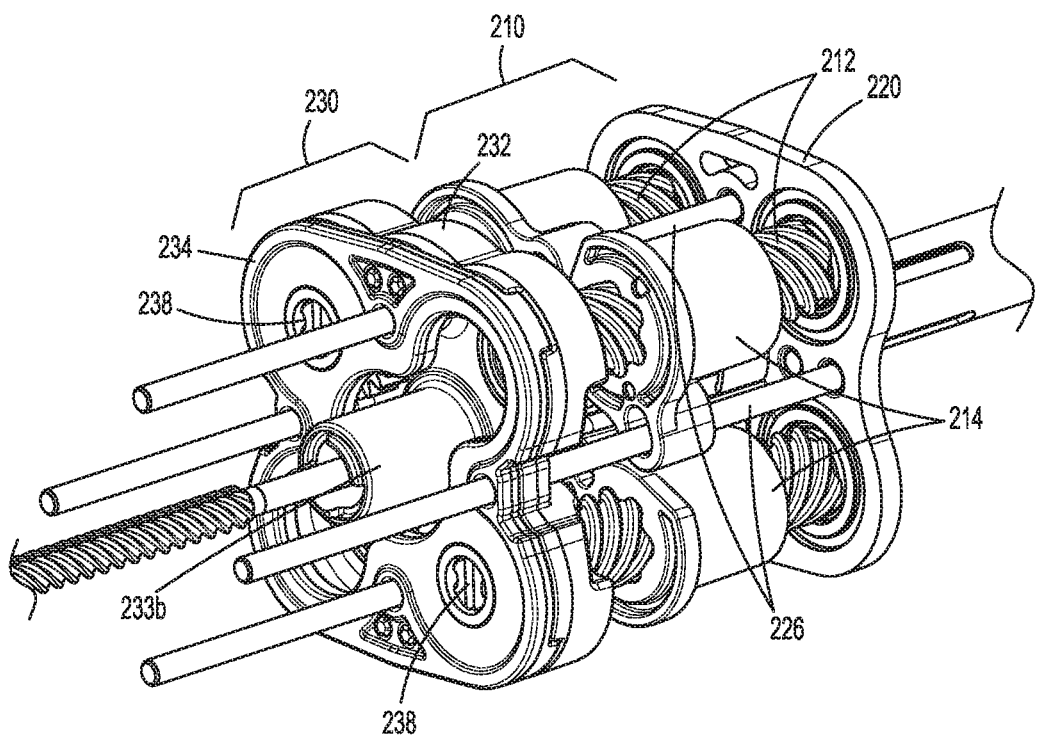
FIG. 9 is a rear, perspective view of the first gear sub-assembly of FIG. 4 assembled on the lead screw sub-assembly of FIG. 7 to partially assemble the articulation assembly.

Turning to FIGS. 7-9, in order to assemble articulation assembly 200, lead screw sub-assembly 210 is assembled with knife tube 62 and drive rod 484 extending therethrough. Next, first gear sub-assembly 230 is inserted about knife tube 62 and drive rod 484, e.g., with knife tube 62 and drive rod 484 extending through central tube 233b of distal housing body 232, and translated distally therealong. First gear sub-assembly 230 may additionally include slots and/or apertures 244 configured to receive dowels 226 of lead screw sub-assembly 210 to thereby guide translation of first gear sub-assembly 230 towards lead screw sub-assembly 210 and inhibit rotation of first gear sub-assembly 230 relative to lead screw sub-assembly 210.

First gear sub-assembly 230 is translated distally about knife tube 62 and drive rod 484 until the proximal end portions 213b of the first diagonally-opposed pair of lead screws 212 are received and engaged within bushings 240 of first gear sub-assembly 230, thereby engaging first gear sub-assembly 230 with lead screw sub-assembly 210, although other engagements are also contemplated. This engagement also rotationally couples the proximal end portions 213b of the first diagonally-opposed pair of lead screws 212 with corresponding keyed outputs 238 of first gear sub-assembly 230, thereby rotatably coupling each of the gears 236 of first gear sub-assembly 230 with one of the lead screws 212 of the first diagonally-opposed pair of lead screws 212. As such, rotation of one of gears 236 rotates the corresponding lead screw 212. The second diagonally-opposed pair of lead screws 212 is engaged within the remaining two bushings 240 and are aligned with the second pair of diagonally-opposed apertures 235d. Further assembly of articulation assembly 200 is detailed below.

Figure 10:
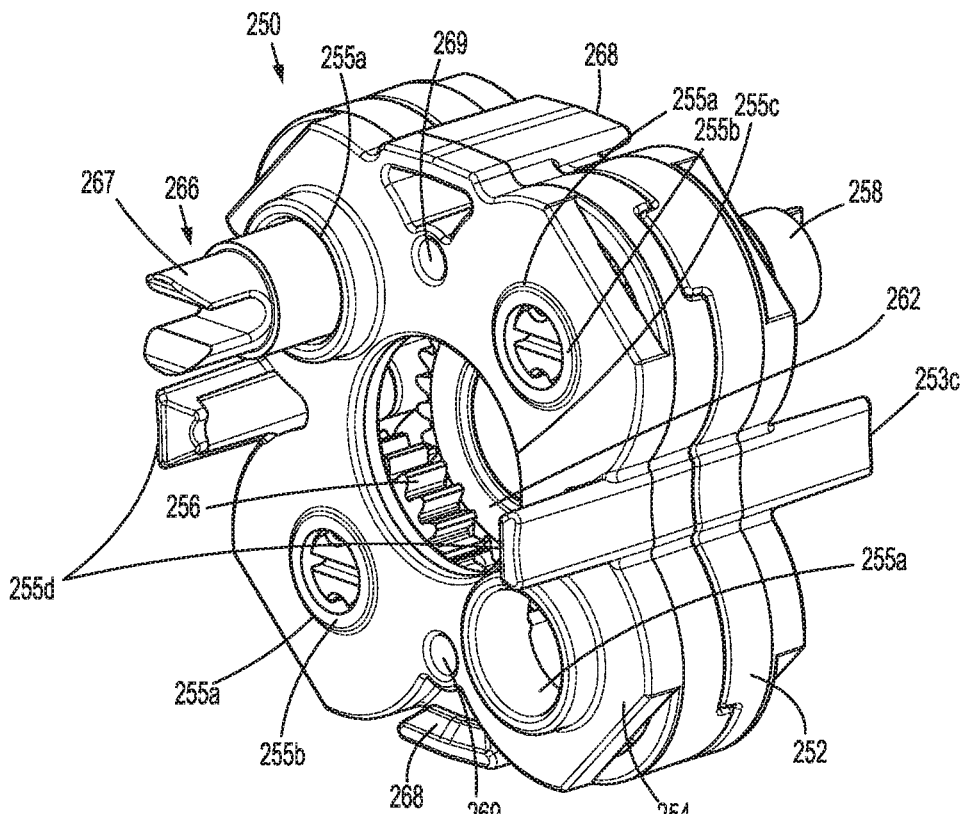
FIG. 10 is a rear, perspective of a second gear sub-assembly of the articulation assembly of the gearbox of the surgical instrument of FIG. 1.
Figure 11:
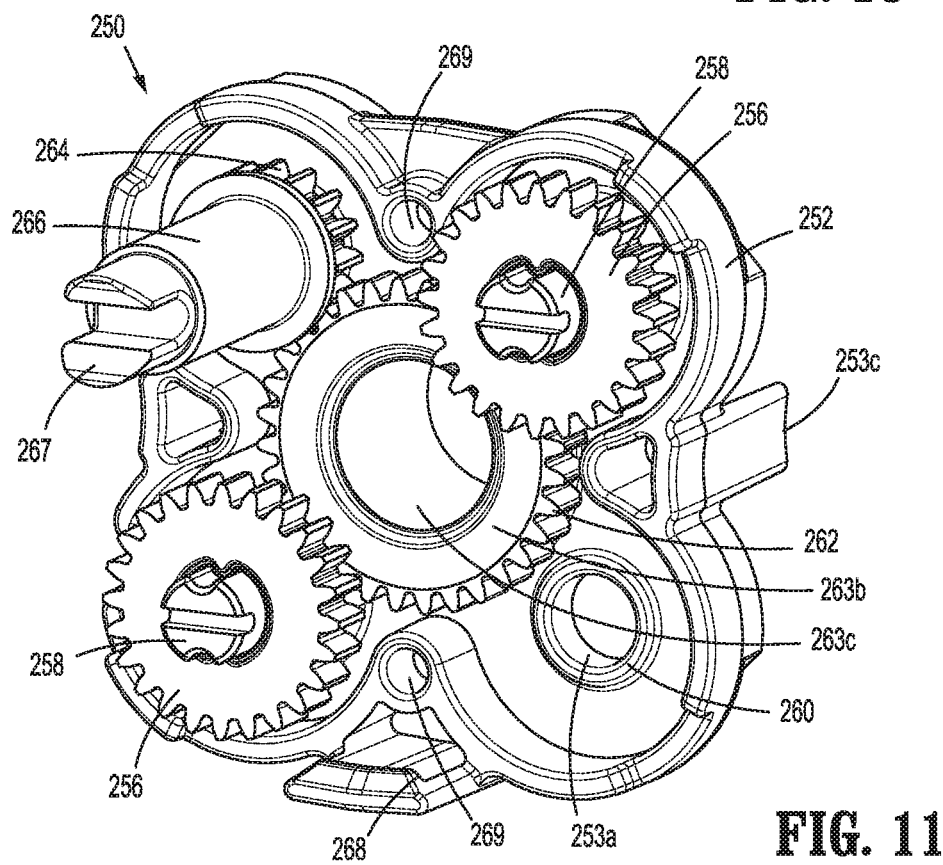
FIG. 11 is a rear, perspective of the second gear sub-assembly of FIG. 10 with the proximal housing body thereof removed.
Figure 12:
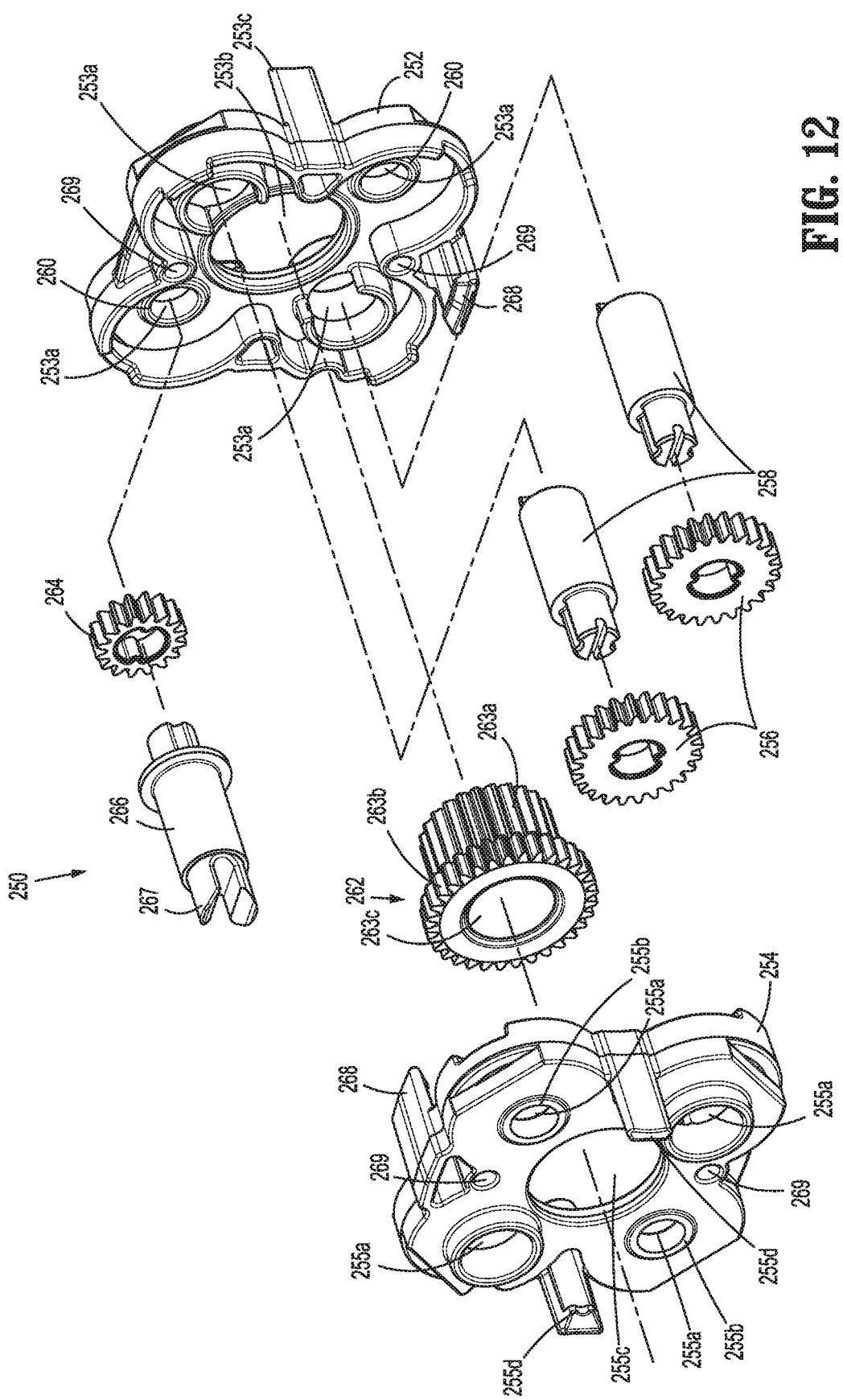
FIG. 12 is an exploded, perspective view of the second gear sub-assembly of FIG. 10.

Referring to FIGS. 10-12, second gear sub-assembly 250 includes a distal housing body 252, a proximal housing body 254, a pair of diagonally-opposed gears 256 mounted on keyed outputs 258, a central compound gear 262, and a first coupling gear 264 mounted on a first coupling shaft 266.

Distal housing body 252 defines four apertures 253a arranged to define a generally square configuration. One pair of diagonally-opposed apertures 253a may include bushings 260 retained therein. Distal housing body 252 further defines a central aperture 253b defined therethrough and a pair of engagement arms 253c extending distally from opposing sides thereof (see also FIG. 13).

Proximal housing body 254 defines four apertures 255a arranged to define a generally square configuration wherein one pair of diagonally-opposed apertures 255a may include bushings 255b retained therein. Proximal housing body 254 further defines a central opening 255c and a pair of engagement arms 255d extending proximally from opposing sides thereof. Distal housing body 252 and proximal housing body 254 include cooperating snap-fit components 268, e.g., on the top and bottom sides thereof, to facilitate engagement of distal housing body 252 and proximal housing body 254 with one another, although other suitable engagements and/or positions thereof are also contemplated.

Keyed outputs 258, which mount diagonally-opposed gears 256 on proximal end portions thereof, are positioned such that the distal end portions thereof extend distally through the diagonally-opposed apertures 253a of distal housing body 252 that do not include bushings 260. The distal end portions of keyed outputs 238 define keyed, e.g., semi-circular, outputs to enable rotational output therefrom. Gears 256 are captured between distal and proximal housing bodies 252, 254 upon engagement thereof.

Central compound gear 262 includes a distal gear 263a and a proximal gear 263b and defines a lumen 263c extending therethrough. Distal gear 263a is configured to extend distally though central opening 253b of distal housing body 252 while proximal gear 263b is configured to be captured between distal and proximal housing bodies 252, 254, respectively, in alignment with central opening 253b of distal housing body 252 and central opening 255c of proximal housing body 254.

First coupling shaft 266 includes a distal end portion upon which first coupling gear 264 is mounted and which extends into one of the bushings 260. A proximal end portion of first coupling shaft 266 extends proximally from first coupling gear 264 and defines a keyed input 267, e.g., a semi-circular configuration, at the proximal end portion thereof. More specifically, first coupling gear 264 is configured to be captured between distal and proximal housing bodies 252, 254, respectively, in meshed engagement with proximal gear 263b of central compound gear 262. The distal end portion of first coupling shaft 266 is configured to extend into one of the bushings 260 and keyed input 267 is configured to extend proximally through one of the apertures 255a of proximal housing body 254 that does not include a bushing 255b.

With respect to further assembly of articulation assembly 200, e.g., once first gear sub-assembly 230 is assembled with lead screw sub-assembly 210 as detailed above, a first diagonal pair of articulation cables 38 (FIGS. 22 and 23) is pre-tensioned. Pre-tensioning articulation cables 38 (FIGS. 22 and 23) facilitates accurate articulation of end effector assembly 40 (FIG. 1) and retention of end effector assembly 40 (FIG. 1) in position (whether articulated or aligned). In order to pre-tension the first diagonal pair of articulation cables 38 (FIGS. 22 and 23), the collars 214 associated with the first opposing diagonal pair of articulation cables 38 (FIGS. 22 and 23) are pulled proximally in a similar manner to tension the corresponding articulation cables 38 (FIGS. 22 and 23) to a pre-tension threshold.

Collars 214 may be translated manually, automatically, or semi-automatically using appropriate fixturing (not shown). A suitable force sensing mechanism (not shown) may be utilized to determine the tension on the pre-tensioned articulation cables 38 (FIGS. 22 and 23) such that the articulation cables 38 (FIGS. 22 and 23) are pre-tensioned to the pre-tension threshold.

Figure 13:
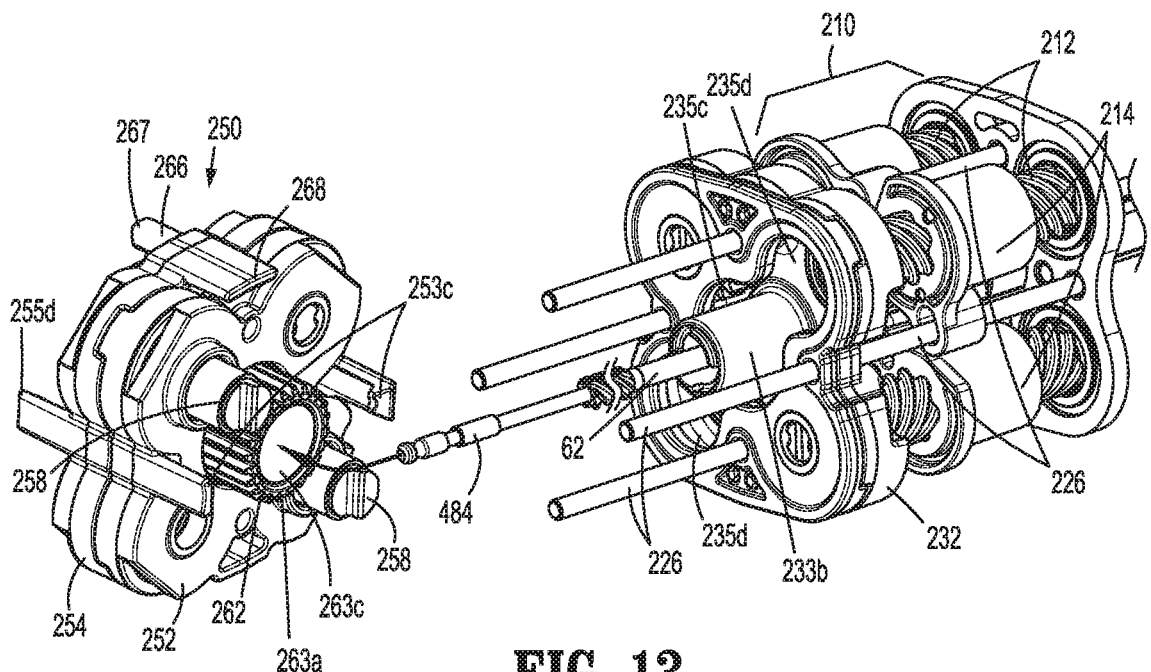
FIG. 13 is an exploded, perspective view illustrating assembly of the second gear sub-assembly of FIG. 10 on the partially-assembled articulation assembly of FIG. 9.
Figure 14:
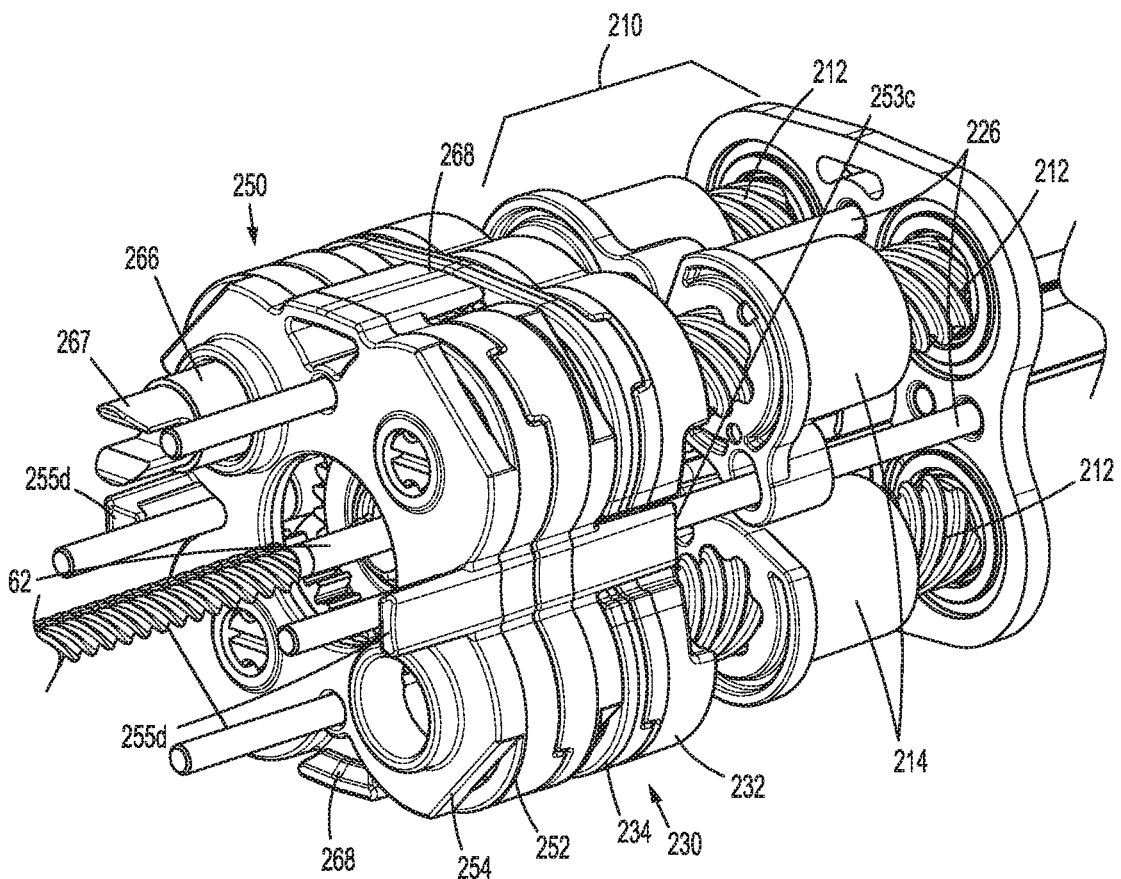
FIG. 14 is a front, perspective view of the second gear sub-assembly of FIG. 10 assembled on the partially-assembled articulation assembly of FIG. 9 to further partially assemble the articulation assembly.

Referring to FIGS. 13 and 14, once the pre-tension threshold for the first diagonal pair of articulation cables 38 (FIGS. 22 and 23) has been reached (and is maintained, e.g., manually, automatically, or semi-automatically using appropriate fixturing (not shown)), second gear sub-assembly 250 is inserted about knife tube 62 and drive rod 484, e.g., with knife tube 62 and drive rod 484 extending through central opening 253b of distal housing body 252, lumen 263c of compound gear 262, and central opening 255c of proximal housing body 254. Second gear sub-assembly 250 may additionally include slots and/or apertures 269 configured to receive dowels 226 of lead screw sub-assembly 210 to thereby guide translation of second gear sub-assembly 250 towards first gear sub-assembly 230 and lead screw sub-assembly 210 and inhibit rotation of second gear sub-assembly 250 relative thereto.

Second gear sub-assembly 250 is translated distally along knife tube 62 and drive rod 484 into abutment with first gear sub-assembly 230, whereby engagement arms 253c of distal housing body 252 snap-into engagement within corresponding recesses defined on opposing outer sides of first gear sub-assembly 230 to thereby engage second gear sub-assembly 250 with first gear sub-assembly 230. Upon this engagement, keyed outputs 258 are rotationally coupled with the proximal end portions 213b of the second diagonally-opposed pair of lead screws 212, thereby rotatably coupling each of the gears 256 of second gear sub-assembly 250 with one of the lead screws 212 of the second diagonally-opposed pair of lead screws 212. As such, rotation of one of gears 256 rotates the corresponding lead screw 212.

Figure 22:
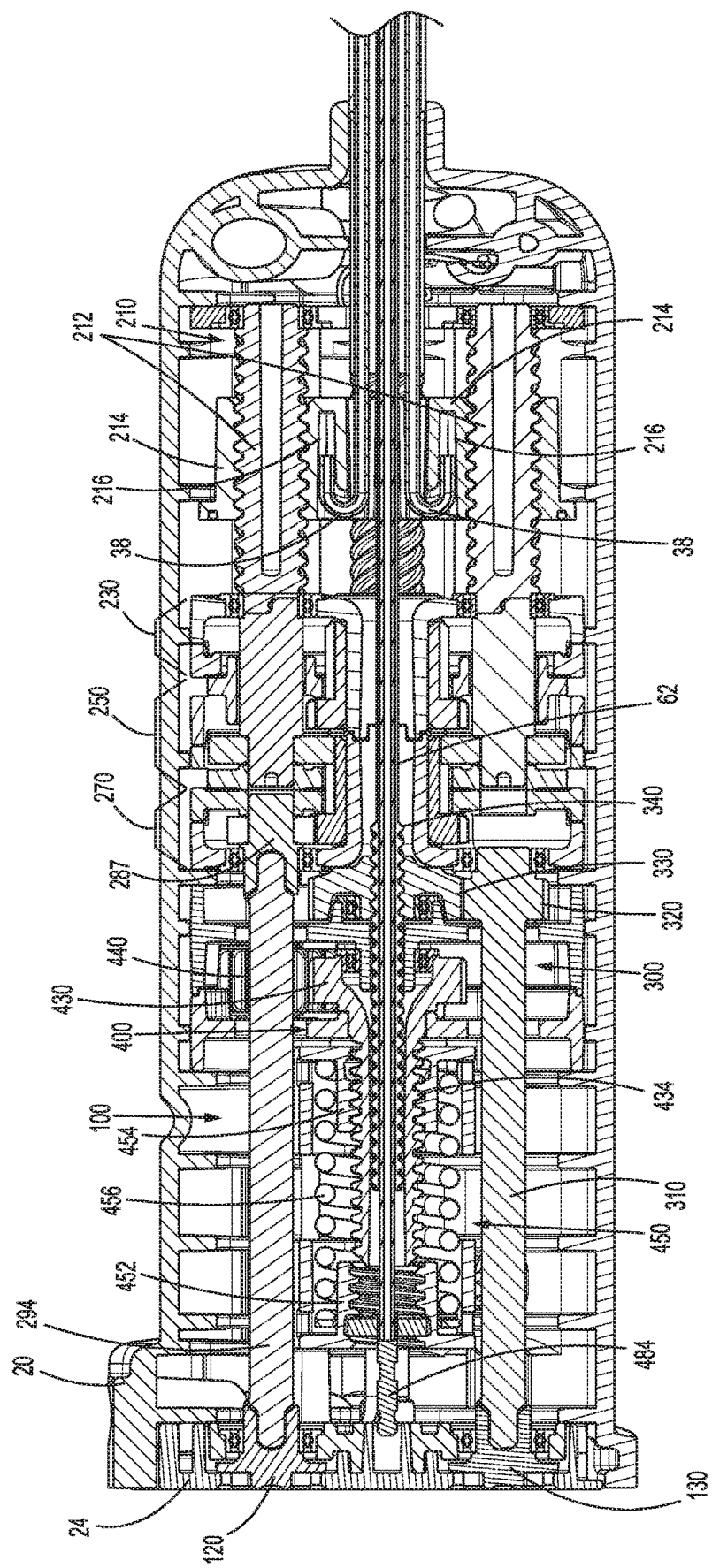
FIG. 22 is a transverse, cross-sectional view taken along section line "22-22" of FIG. 3.
Figure 23:
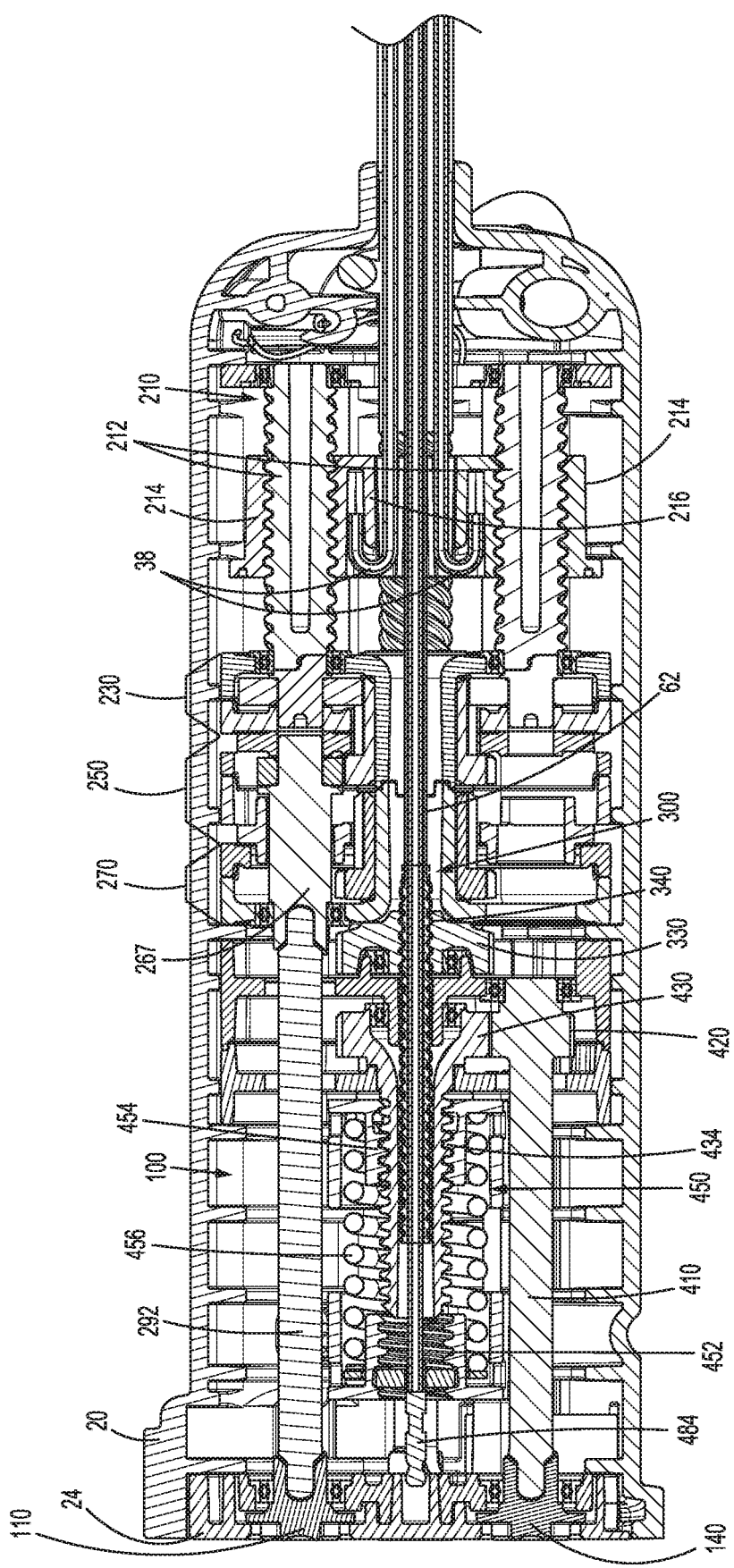
FIG. 23 is a transverse, cross-sectional view taken along section line "23-23" of FIG. 3.

Engagement of second gear sub-assembly 250 with first gear sub-assembly 230 also moves distal gear 263a of central compound gear 262 through central opening 235c of proximal housing body 234 of first gear sub-assembly 230 and about central tube 233b of distal housing body 232 of first gear sub-assembly 230 into meshed engagement with and between diagonally-opposed gears 236 of first gear sub-assembly 230. In this manner, engagement of second gear sub-assembly 250 with first gear sub-assembly 230 couples the diagonally-opposed gears 236 with one another, thereby coupling the lead screws 212 of the first diagonally-opposed pair of lead screws 212, e.g., the lead screws coupled to diagonally-opposed gears 236, with one another. These lead screws 212, more specifically, are the lead screws 212 whose collars 214 were previously moved to tension the corresponding articulation cables 38 (FIGS. 22 and 23). Because these articulation cables 38 (FIGS. 22 and 23) were pre-tensioned in the same direction, since diagonally-opposed lead screws 212 define opposite pitch, and due to the fact that distal gear 263a of central compound gear 262 is engaged with diagonally-opposed gears 236, the pre-tension on these articulation cables 38 (FIGS. 22 and 23) is retained upon engagement of distal gear 263a with diagonally-opposed gears 236 and, thus, the manually retention, fixturing, or other mechanical utilized to maintain the pre-tension can be released while articulation cables 38 (FIGS. 22 and 23) remain pre-tensioned. Still further assembly of articulation assembly 200 is detailed below.

Figure 15:
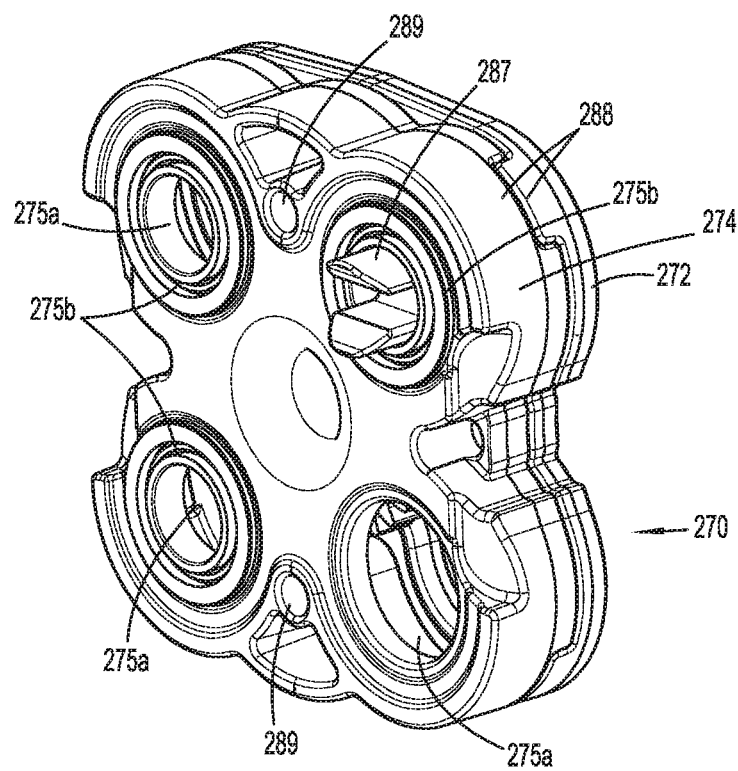
FIG. 15 is a rear, perspective view of a third gear sub-assembly of the articulation assembly of the gearbox of the surgical instrument of FIG. 1.
Figure 16:
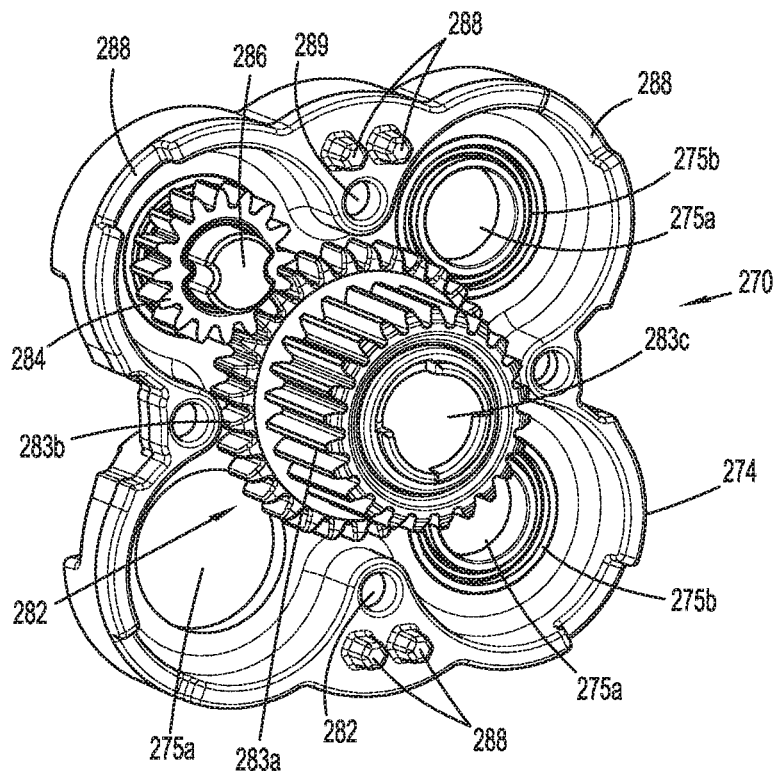
FIG. 16 is a front, perspective of the third gear sub-assembly of FIG. 15 with the distal housing body thereof removed.
Figure 17:
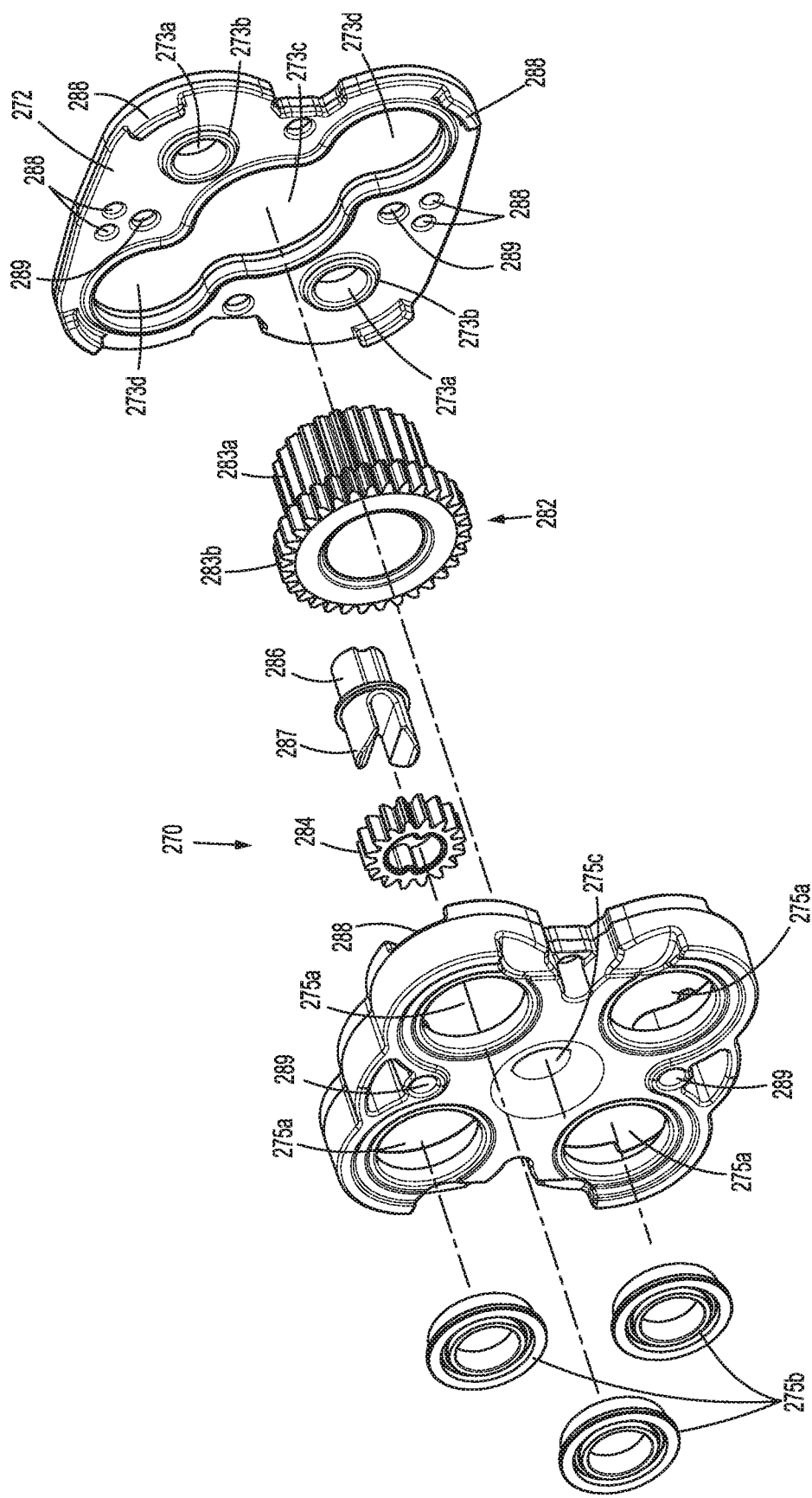
FIG. 17 is an exploded, perspective view of the third gear sub-assembly of FIG. 15.

Turning to FIGS. 15-17, third gear sub-assembly 270 includes a distal housing body 272, a proximal housing body 274, a central compound gear 282, and a second coupling gear 284 mounted on a second coupling shaft 286. Distal housing body 272 defines a pair of diagonally-opposed apertures 273a each of which may include a bushing 273b disposed therein. Distal housing body 272 further defines a central opening 273*c* and a second pair of diagonally-opposed apertures 273*d* (which may communicate with central opening 273*c* as shown or may be separate therefrom).

Proximal housing body 274 defines four apertures 275*a* arranged to define a generally square configuration wherein three of the four apertures 275*a* may include bushings 275*b* retained therein. Proximal housing body 274 further defines a central opening 275*c*. Distal housing body 272 and proximal housing body 274 include cooperating male-female components 288 to facilitate engagement of distal housing body 272 and proximal housing body 274 with one another, although other suitable engagements are also contemplated.

Central compound gear 282 includes a distal gear 283*a* and a proximal gear 283*b* and defines a lumen 283*c* extending therethrough. Distal gear 283*a* is configured to extend distally though central opening 273*c* of distal housing body 252 while proximal gear 283*b* is configured to be captured between distal and proximal housing bodies 272, 274, respectively, in alignment with central opening 273*c* of distal housing body 272 and central opening 275*c* of proximal housing body 274.

Second coupling shaft 286 includes second coupling gear 284 mounted thereon and has a proximal end portion that defines a keyed input 287, e.g., a semi-circular configuration. Second coupling gear 284 is configured to be captured between distal and proximal housing bodies 272, 274, respectively, in meshed engagement with proximal gear 283*b* of central compound gear 282. Keyed input 287 is configured to extend proximally through the aperture 275*a* of proximal housing body 274 that does not include a bushing 275*b*.

With respect to further assembly of articulation assembly 200, e.g., once second gear sub-assembly 250 is assembled with first gear sub-assembly 230 and lead screw sub-assembly 210 as detailed above, the second diagonal pair of articulation cables 38 (FIGS. 22 and 23) is pre-tensioned similarly as detailed above with respect to the first diagonal pair of articulation cables 38 (FIGS. 22 and 23).

Figure 18:
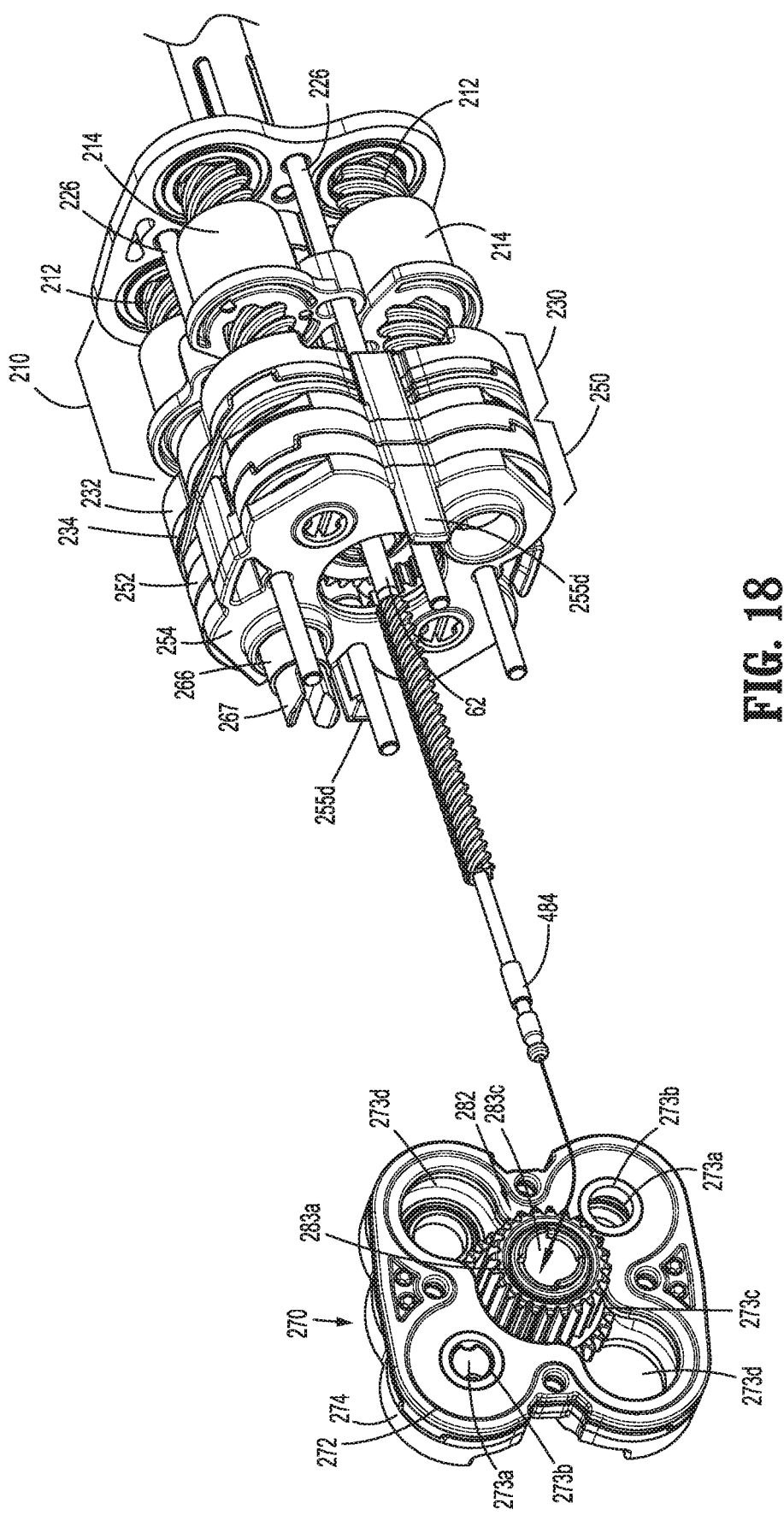
FIG. 18 is an exploded, perspective view illustrating assembly of the third gear sub-assembly of FIG. 15 on the further partially assembled articulation assembly of FIG. 14.
Figure 19:
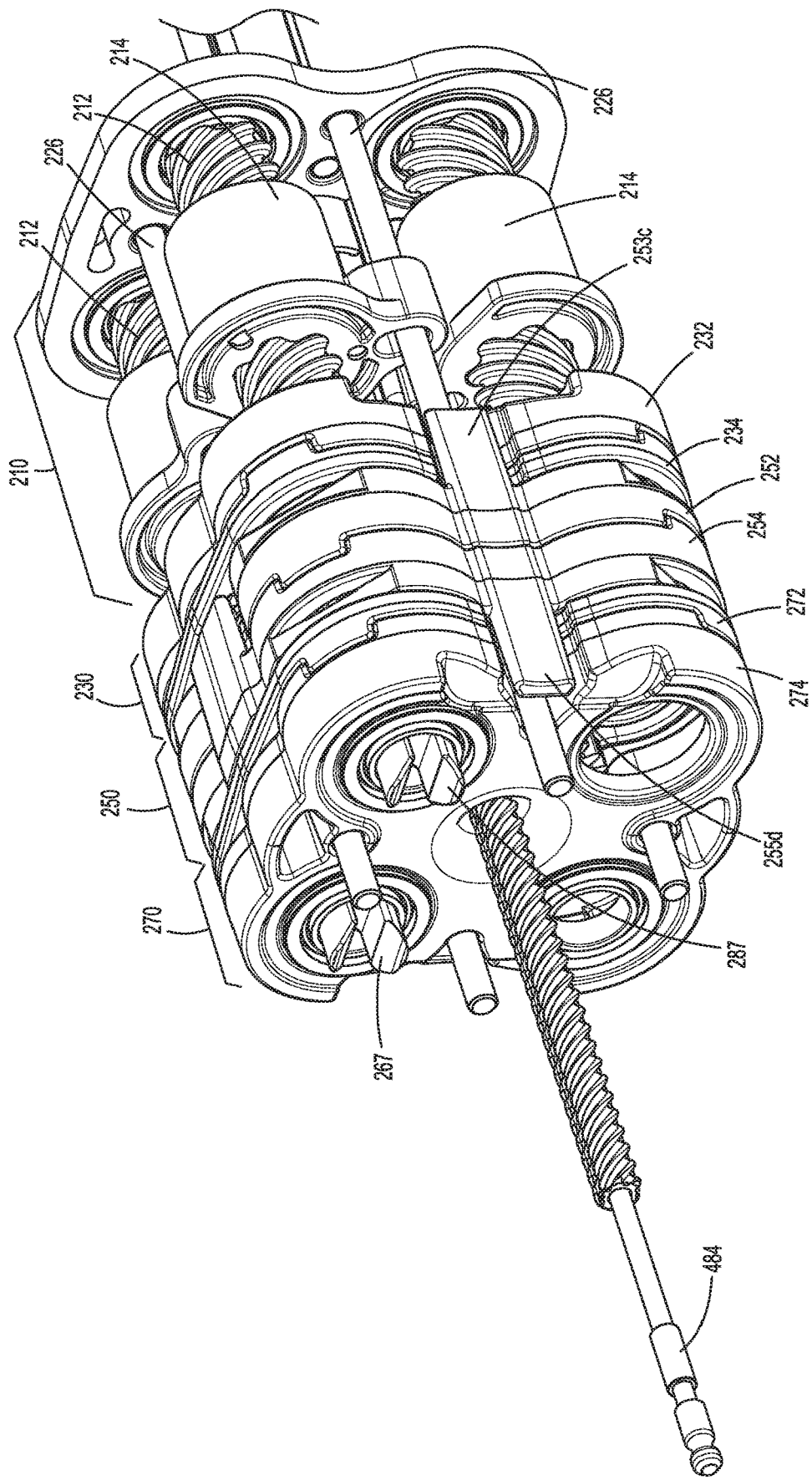
FIG. 19 is a front, perspective view of the third gear sub-assembly of FIG. 15 assembled on the further partially assembled articulation assembly of FIG. 14 to complete assembly of the articulation assembly.
Figure 20:
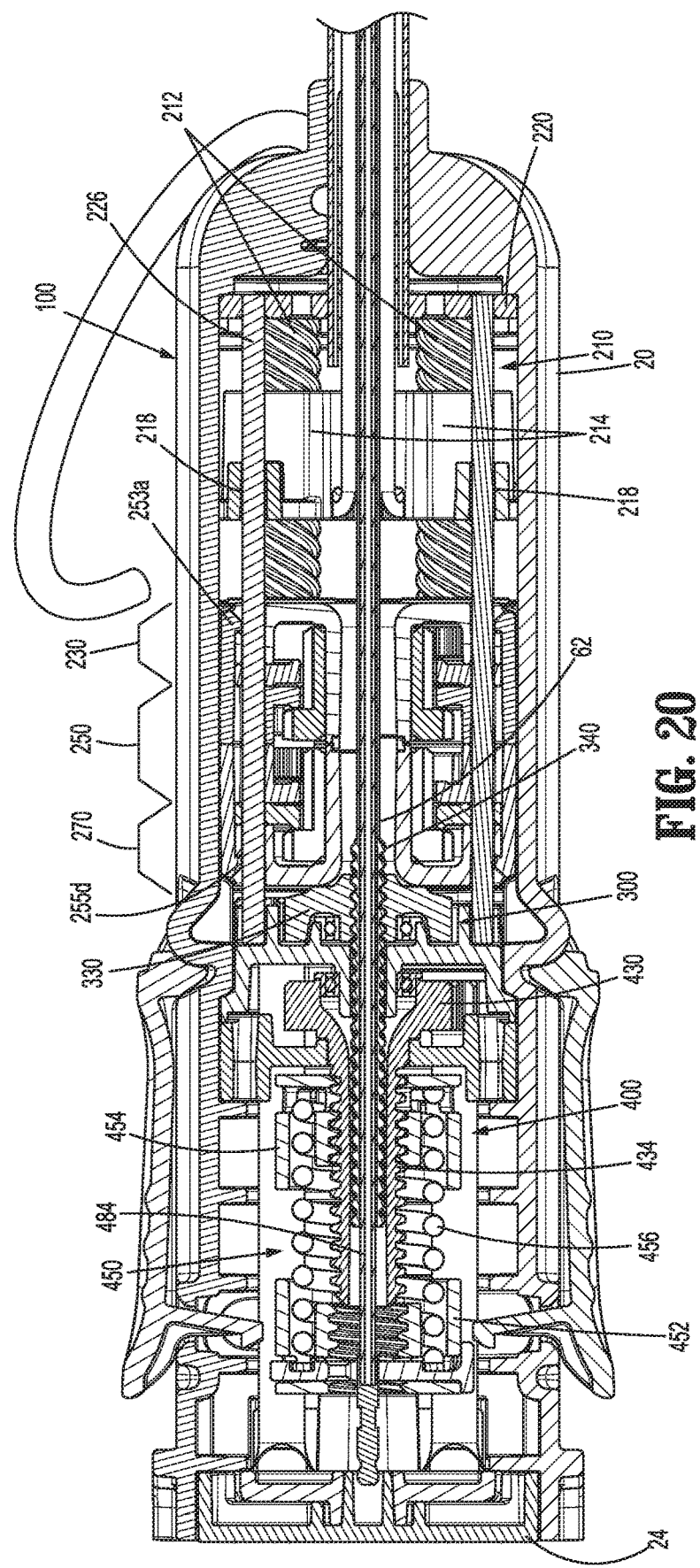
FIG. 20 is a longitudinal, cross-sectional view taken along section line "20-20" of FIG. 1.
Figure 21:
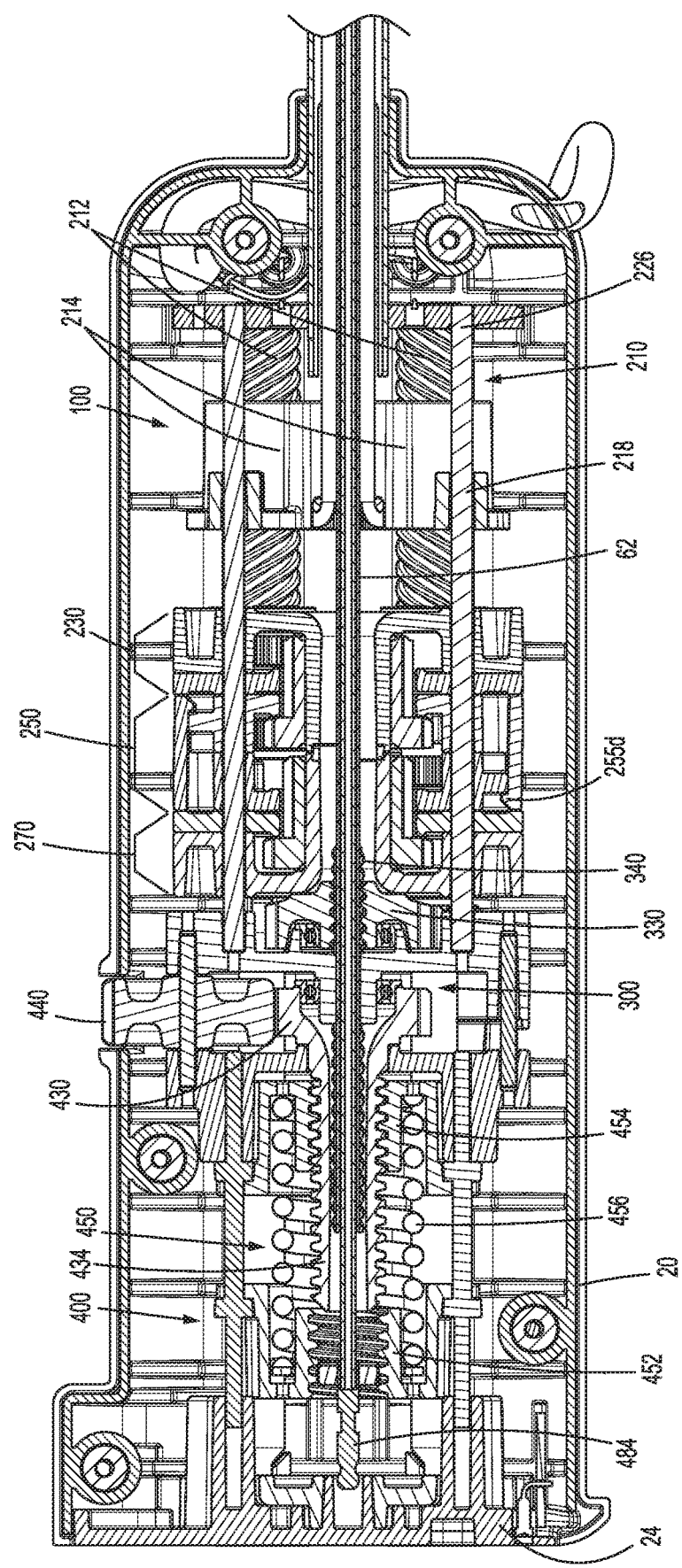
FIG. 21 is a longitudinal, cross-sectional view taken along section line "21-21" of FIG. 1.

Referring to FIGS. 18 and 19, once the pre-tension threshold for the second diagonal pair of articulation cables 38 (FIGS. 22 and 23) has been reached (and is maintained, e.g., manually, automatically, or semi-automatically using appropriate fixturing (not shown)), third gear sub-assembly 270 is inserted about knife tube 62 and drive rod 484, e.g., with knife tube 62 and drive rod 484 extending through central opening 273*c* of distal housing body 272, lumen 283*c* of compound gear 282, and central opening 275*c* of proximal housing body 274. Third gear sub-assembly 270 may additionally include slots and/or apertures 289 configured to receive dowels 226 of lead screw sub-assembly 210 to thereby guide translation of third gear sub-assembly 270 towards first and second gear sub-assemblies 230, 250 and lead screw sub-assembly 210 and inhibit rotation of third gear sub-assembly 270 relative thereto.

Third gear sub-assembly 270 is translated distally along knife tube 62 and drive rod 484 into abutment with second gear sub-assembly 250, whereby engagement arms 255*d* of proximal housing body 252 of second gear sub-assembly 250 snap-into engagement within corresponding recesses defined on opposing outer sides of third gear sub-assembly 270 to thereby engage third gear sub-assembly 270 with second gear sub-assembly 250.

Upon this engagement, keyed input 267 of first coupling shaft 266 extends through one of the second diagonally-opposed apertures 273*d* of distal housing body 272 and the bushings 275*b* disposed within the corresponding aligned aperture 275*a* of proximal housing body 274 to extend proximally from third gear sub-assembly 270. Further, distal gear 283*a* of central compound gear 282 is inserted through central opening 255*c* of proximal housing body 254 and into meshed engagement with and between diagonally-opposed gears 256 of second gear sub-assembly 250.

In this manner, engagement of third gear sub-assembly 270 couples the diagonally-opposed gears 256 with one another, thereby coupling the second diagonally-opposed pair of lead screws 212, e.g., the lead screws coupled to diagonally-opposed gears 236, with one another. These lead screws 212, more specifically, are the lead screws 212 whose articulation cables 38 (FIGS. 22 and 23) were pre-tensioned after installation of second gear sub-assembly 250 but prior to installation of third gear sub-assembly 270. Because these articulation cables 38 (FIGS. 22 and 23) were pre-tensioned in the same direction, since diagonally-opposed lead screws 212 define opposite pitch, and due to the fact that distal gear 283*a* of central compound gear 282 is engaged with diagonally-opposed gears 256, the pre-tension on these articulation cables 38 (FIGS. 22 and 23) is retained upon engagement of distal gear 283*a* of central compound gear 282 with diagonally-opposed gears 256 and, thus, the manually retention, fixturing, or other mechanical utilized to maintain the pre-tension can be release while articulation cables 38 (FIGS. 22 and 23) remain pre-tensioned. As such, both pairs of, e.g., all four, articulation cables 38 (FIGS. 22 and 23) are now maintained in their pre-tensioned states.

Referring also to FIGS. 2A, 2B, 22, and 23, with first, second, and third gear sub-assemblies 230, 250, 270, respectively, assembled with one another and lead screw sub-assembly 210, as detailed above, input shafts 292, 294 can be connected between inputs 110, 120 and keyed inputs 267, 287, respectively. Thus, in use, rotational input provided to inputs 110, 120 can be utilized to move collars 214 about lead screws 212 in diagonal pairs. Depending upon the direction of rotational input provided to inputs 110, 120 and whether the inputs to the pairs are the same or opposite, pitch articulation (in either direction), yaw articulation (in either direction), and/or any combination thereof can be achieved.

Once articulation assembly 200 is assembled as detailed above, and prior to or after coupling articulation assembly 200 with inputs 110, 120, knife drive assembly 300 (detailed below) is operably coupled between input 130 and knife tube 62 and jaw drive assembly 400 (also detailed below) is operably coupled between input 140 and drive rod 484. Once this is completed, first and second body portion 22*a*, 22*b* of housing 20 and proximal face plate 24 may be engaged with one another to enclose the assembled gearbox 100.

Turning to FIGS. 1-2B and 20-23, knife drive assembly 300 includes an input shaft 310, an input gear 320 engaged on input shaft 310, a central gear 330 defining external threading disposed in meshed engagement with input gear 320 and internal threading, and a lead screw 340 extending through the central gear 330 in meshed engagement with the internal threading thereof. As a result of this configuration, a rotational input provided to third input 130 rotates input shaft 310, thereby rotating input gear 320 to, in turn, rotate central gear 330, which results in translation of lead screw 340. Lead screw 340 is fixedly engaged about a proximal end portion of knife tube 62 such that translation of lead screw 340 translates knife tube 62, e.g., to thereby translate the knife blade (not shown) between jaw members 42, 44 (FIG. 1) to cut tissue grasped therebetween. Lead screw 340 and knife tube 62 are coaxially disposed about drive rod 484.

Continuing with reference to FIGS. 1-2B and 20-23, jaw drive assembly 400 includes an input shaft 410 operably coupled to fourth input 140 at a proximal end portion thereof, an input gear 420 fixedly engaged on input shaft 410 at a distal end portion thereof, a drive gear 430 disposed in meshed engagement with input gear 420, a thumbwheel 440 disposed in meshed engagement with drive gear 430, a lead screw 434 is fixedly engaged, e.g., monolithically formed with, drive gear 430, and a spring force assembly 450 operably coupling lead screw 434 with drive rod 484. Spring force assembly 450, more specifically, includes a proximal hub 452 engaged with a proximal end portion of drive rod 484, a distal hub 454 threadingly engaged about lead screw 434, and a compression spring 456 disposed between proximal and distal hubs 452, 454, respectively.

As a result of the above-detailed configuration, in response to an input to close end effector assembly 40, e.g., rotational input to fourth input 140 or a manual input to rotation wheel 440, drive shaft 410 is rotated to thereby rotate input gear 420 which, in turn, rotates drive gear 430 such that distal hub 454 is translated proximally towards proximal hub 452. Initially, where forces resisting approximation of jaw members 42, 44 are below a threshold corresponding to the spring value of compression spring 456, the closure force applied by jaw members 42, 44 is relatively low such that the urging of distal hub 454 proximally against compression spring 456 urges compression spring 456 proximally which, in turn, urges drive rod 484 proximally to pivot jaw member 42 relative to jaw member 44 from the spaced-apart position towards the approximated position to grasp tissue therebetween.

Upon further approximation of jaw members 42, 44 to grasp tissue therebetween, the forces resisting approximation of jaw members 42, 44, e.g., tissue resisting compression, may reach the threshold and, thus the closure force applied by jaw members 42, 44 may reach a corresponding threshold. In order to maintain the closure force applied by jaw members 42, 44 within a closure force range such as, for example, from about 3 kg/cm$^2$ to about 16 kg/cm$^2$, application of further closure force by jaw members 42, 44 is inhibited beyond this point despite further rotational input to fourth input 140. More specifically, once the threshold has been reached, further rotational input to fourth input 140 rotates drive shaft 410, input gear 420, and drive gear 430 to translate distal hub 454 further proximally into compression spring 456. However, rather than compression spring 456 urging proximal hub 452 further proximally to continue approximation of jaw members 42, 44 and increase the closure force applied therebetween, compression spring 456 is compressed, enabling proximal hub 452 and, thus, drive rod 484 to remain in position despite the continued movement of distal hub 454, thus inhibiting application of additional closure force between jaw members 42, 44.

With tissue grasped between jaw members 42, 44 under an appropriate closure force, energy may be supplied to jaw members 42, 44 to treat, e.g., seal tissue. Thereafter, the knife blade (not shown) may be advanced between jaw members 42, 44 to cut the treated tissue, as detailed above.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. An articulation assembly for a surgical instrument, comprising:

a lead screw sub-assembly including first, second, third, and fourth lead screws, the first and third lead screws diagonally-opposite one another and the second and fourth lead screws diagonally-opposite one another;

a first gear sub-assembly including a first housing at least partially capturing first and second gears therein, the first and second gears coupled to the first and third lead screws;

a second gear sub-assembly configured to engage the first gear sub-assembly, the second gear sub-assembly including a second housing at least partially capturing third and fourth gears, a first central compound gear, and a first coupling gear disposed about a first input, the third and fourth gears coupled to the second and fourth lead screws, respectively, the first central compound gear including a distal gear and a proximal gear, the distal gear coupling the first and second gears with one another, thereby coupling the first and third lead screws with one another, the first coupling gear coupled with the proximal gear, the first input extending proximally from the second housing; and a third gear sub-assembly configured to engage the second gear sub-assembly, the third gear sub-assembly including a third housing at least partially capturing a second central compound gear and a second coupling gear disposed about a second input, the second central compound gear including a distal gear and a proximal gear, the distal gear coupling the third and fourth gears with one another, thereby coupling the second and fourth lead screws with one another, the second coupling gear coupled with the proximal gear, the second input extending proximally from the third housing, wherein the first input extends proximally through and from the third housing;

wherein a rotational input provided to the first input rotates the first and third lead screws, and wherein a rotational input provided to the second input rotates the second and fourth lead screws.

2. The articulation assembly according to claim 1, wherein each of the first, second, third, and fourth lead screws includes a collar engaged thereon and an articulation cable coupled to the collar, wherein rotation of one of the first, second, third, or fourth lead screws translates the corresponding collar to tension or un-tension the corresponding articulation cable.

3. The articulation assembly according to claim 2, wherein the first and third lead screws define opposite pitch such that a rotational input provided to the first input tensions one of the corresponding articulation cables and un-tensions the other corresponding articulation cable, and wherein the second and fourth lead screws define opposite pitch such that a rotational input provided to the second input tensions one of the corresponding articulation cables and un-tensions the other corresponding articulation cable.

4. The articulation assembly according to claim 1, wherein the first housing of the first gear sub-assembly includes proximal and distal housing bodies at least partially capturing the first and second gears therebetween.

5. The articulation assembly according to claim 1, wherein the first and second gears are coupled to the first and third lead screws via respective first and second outputs engaged with the first and second gears, respectively, and extending distally from the first housing to couple to the first and third lead screws.

6. The articulation assembly according to claim 1, wherein the second housing of the second gear sub-assembly includes proximal and distal housing bodies at least partially capturing the third and fourth gears, the first central compound gear, and the first coupling gear therebetween.

7. The articulation assembly according to claim 1, wherein the third and fourth gears are coupled to the second and fourth lead screws via respective third and fourth outputs engaged with the third and fourth gears, respectively, and extending distally from the second housing body through the first housing to couple to the second and fourth lead screws.

8. The articulation assembly according to claim 1, wherein the third housing of the third gear sub-assembly includes proximal and distal housing bodies at least partially capturing the second central compound gear and the second coupling gear therebetween.

9. The articulation assembly according to claim 1, wherein the first, second, and third housings are configured to stack relatively to one another in a distal-to-proximal orientation.

10. The articulation assembly according to claim 1, wherein at least one first engagement arm engages the first and second housings with one another, and wherein at least one second engagement arm engages the second and third housings with one another.

11. An articulation mechanism for a surgical instrument, comprising:
 a lead screw sub-assembly including first, second, third, and fourth lead screws, the first and third lead screws defining opposite pitch and diagonally-opposite one another and the second and fourth lead screws defining opposite pitch and diagonally-opposite one another, each of the first, second, third, and fourth lead screws including a collar engaged thereon and an articulation cable coupled to the collar, wherein rotation of one of the first, second, third, or fourth lead screws translates the corresponding collar to tension or un-tension the corresponding articulation cable;
 a first gear sub-assembly including first and second gears disposed about first and second outputs, respectively, and proximal and distal housing bodies capturing the first and second gears therebetween, wherein the first and second outputs extend distally from the distal housing body to couple to the first and third lead screws;
 a second gear sub-assembly configured to engage the first gear sub-assembly, the second gear sub-assembly including third and fourth gears disposed about third and fourth outputs, respectively, a first central compound gear, a first coupling gear disposed about a first input, and proximal and distal housing bodies at least partially capturing the third and fourth gears, the first central compound gear, and the first coupling gear therebetween, wherein the third and fourth outputs extend distally from the distal housing body of the second gear sub-assembly and through the first gear sub-assembly to couple to the second and fourth lead screws, respectively, the first central compound gear including a distal gear and a proximal gear, the distal gear configured to extend into the first gear sub-assembly and engage the first and second gears with one another, thereby coupling the first and third lead screws with one another, the first coupling gear coupled with the proximal gear, the first input extending proximally from the proximal housing body of the second gear sub-assembly; and
 a third gear sub-assembly configured to engage the second gear sub-assembly, the third gear sub-assembly including a second central compound gear, a second coupling gear disposed about a second input, and proximal and distal housing bodies at least partially capturing the second compound gear and the second coupling gear therebetween, the second central compound gear including a distal gear and a proximal gear, the distal gear configured to extend into the second gear sub-assembly and engage the third and fourth gears with one another, thereby coupling the second and fourth lead screws with one another, the second coupling gear coupled with the proximal gear, the second input extending proximally from the proximal housing body of the third gear sub-assembly, wherein the first input extends proximally through and from the third gear sub-assembly,
 wherein a rotational input provided to the first input rotates the first and second lead screws to tension or un-tension the first and third articulation cables, and wherein a rotational input provided to the second input rotates the second and fourth lead screws to tension or un-tension the second and fourth articulation cables.

12. The articulation assembly according to claim 11, further comprising a plurality of dowels extending through the collars and the first, second and third gear sub-assemblies.

13. The articulation assembly according to claim 11, wherein the lead screw assembly further includes a distal plate, the plurality of dowels engaged with the distal plate.

* * * * *